(12) United States Patent
Northrup

(10) Patent No.: US 6,602,473 B1
(45) Date of Patent: *Aug. 5, 2003

(54) TEMPERATURE CONTROL APPARATUS

(75) Inventor: M. Allen Northrup, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/545,440

(22) Filed: Apr. 7, 2000

Related U.S. Application Data

(63) Continuation of application No. 08/763,465, filed on Dec. 11, 1996, now Pat. No. 6,524,532, which is a continuation-in-part of application No. 08/492,678, filed on Jun. 20, 1995, now Pat. No. 5,589,136.

(51) Int. Cl.[7] .................................................. B01L 3/00
(52) U.S. Cl. ................. 422/102; 422/82.01; 422/82.05; 422/82.09; 422/52; 435/287.1; 435/288.3
(58) Field of Search ........................ 422/52, 58, 82.05, 422/82.09, 102, 129, 240, 241, 131, 82.01; 435/285.1, 292.1, 287.1, 288.3; 935/88

(56) References Cited

U.S. PATENT DOCUMENTS 5,460,780 A 10/1995 Devaney, Jr. ................. 422/99

FOREIGN PATENT DOCUMENTS

| EP | 0436995 A2 | 7/1991 | ........... G01N/35/06 |
| EP | 0603411 A1 | 6/1994 | ............. C12M/1/38 |
| EP | 06623245 A1 | 7/1995 | ............. B01L/7/00 |

Primary Examiner—Jill Warden
Assistant Examiner—Sam P. Siefke
(74) Attorney, Agent, or Firm—L. E. Carnahan; Alan H. Thompson

(57) ABSTRACT

A silicon-based sleeve type chemical reaction chamber that combines heaters, such as doped polysilicon for heating, and bulk silicon for convection cooling. The reaction chamber combines a critical ratio of silicon and non-silicon based materials to provide the thermal properties desired. For example, the chamber may combine a critical ratio of silicon and silicon nitride to the volume of material to be heated (e.g., a liquid) in order to provide uniform heating, yet low power requirements. The reaction chamber will also allow the introduction of a secondary tube (e.g., plastic) into the reaction sleeve that contains the reaction mixture thereby alleviating any potential materials incompatibility issues. The reaction chamber may be utilized in any chemical reaction system for synthesis or processing of organic, inorganic, or biochemical reactions, such as the polymerase chain reaction (PCR) and/or other DNA reactions, such as the ligase chain reaction, which are examples of a synthetic, thermal-cycling-based reaction. The reaction chamber may also be used in synthesis instruments, particularly those for DNA amplification and synthesis.

46 Claims, 17 Drawing Sheets

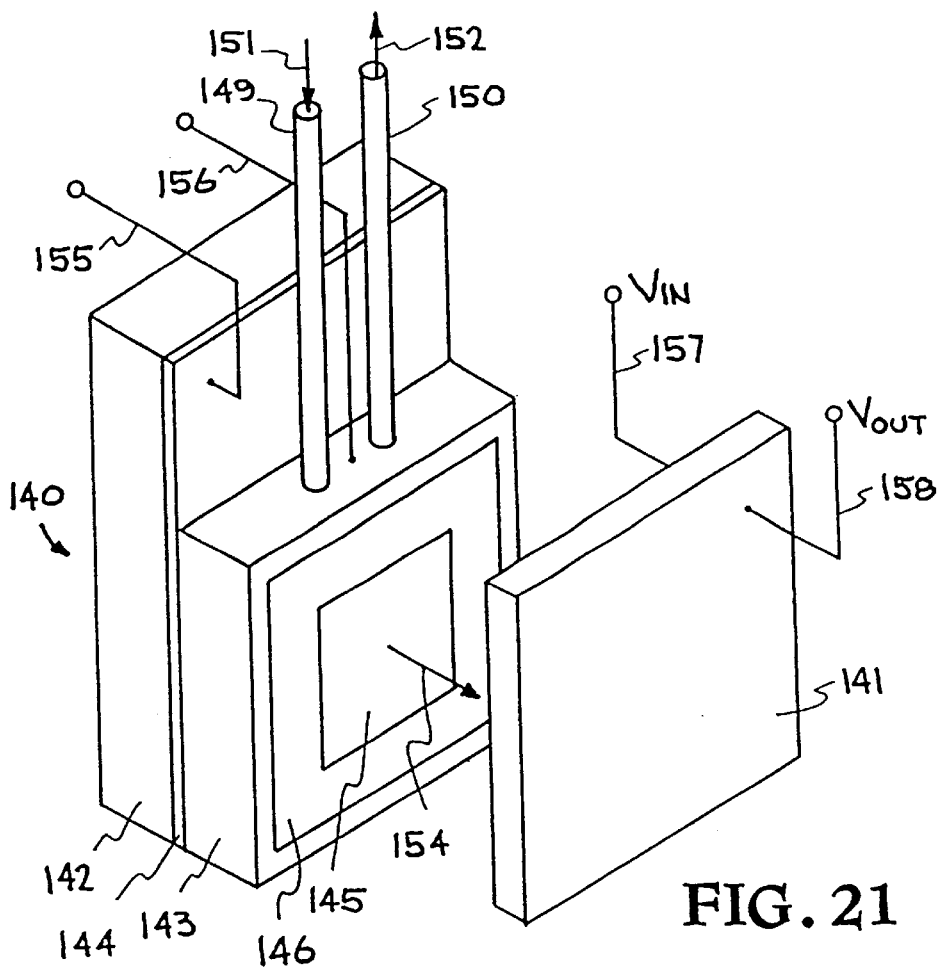
FIG. 21
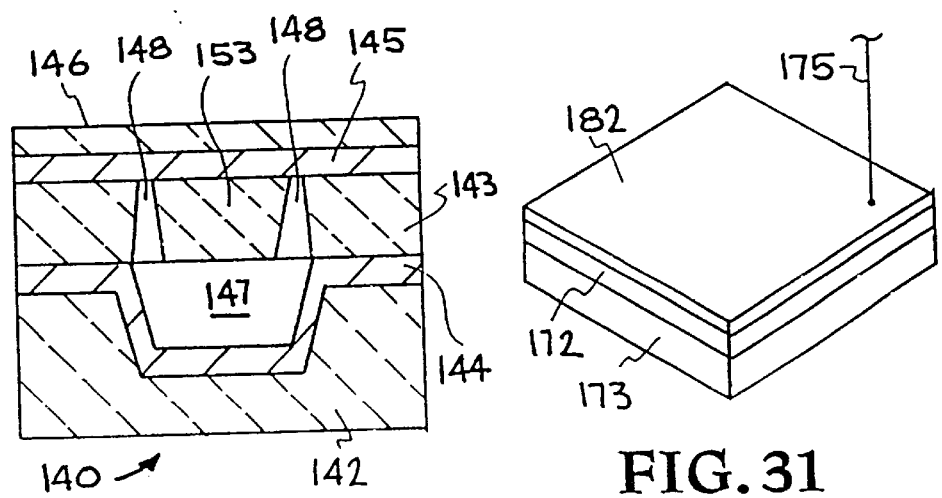
FIG. 22
FIG. 31

TEMPERATURE CONTROL APPARATUS

RELATED APPLICATION

This application is a continuation of 08/763,465 filed Dec. 11, 1996 now U.S. Pat. No. 6,524,532, which is a continuation-in-part of U.S. application Ser. No. 08/492,678, filed Jun. 20, 1995.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to instruments for chemical reaction control and detection of participating reactants and resultant products, particularly to integrated microfabricated instruments for performing microscale chemical reactions involving precise control of parameters of the reactions, and more particularly to silicon-based and non-silicon based sleeve devices as reaction chambers for chemical reactions and which can be utilized in large arrays of individual chambers for a high-throughput microreaction unit.

Current instruments for performing chemical synthesis through thermal control and cycling are generally very large (table-top) and inefficient, and often they work by heating and cooling of a large thermal mass (e.g., an aluminum block). In recent years efforts have been directed to miniaturization of these instruments by designing and constructing reaction chambers out of silicon and silicon-based materials (e.g., silicon, nitride, polycrystalline silicon) that have integrated heaters and cooling via convection through the silicon.

Microfabrication technologies are now well known and include sputtering, electrode position, low-pressure vapor deposition, photolithography, and etching. These and similar processes can be applied to the fabrication of reaction chambers and their control elements such as heaters, thermocouples, detectors, sensors, electrodes, and other devices that can be used to sense and control the reaction parameters. Examples include magnetic films, thermoelectric films, and electroactive films for reagent manipulation. Additional fabrication techniques include evaporation, extrusion, casting, sintering, injection, forming, pulling, laminating, etc. can be used to microfabricate reaction chambers out of a variety of appropriate materials. Microfabricated devices are formed, for example, on crystalline substrates, such as silicon and gallium arsenide, but may be formed on non-crystalline materials, such as glass, ceramic, metals, or certain polymers. The shapes of crystalline silicon devices, for example, can be precisely controlled since etched surfaces are generally crystal planes, and crystalline materials may be bonded by processes such as fusion at elevated temperatures, anodic bonding, or field-assisted methods.

Monolithic microfabrication technology now enables the production of electrical, mechanical, electromechanical, optical, chemical and thermal devices, including pumps, valves, heaters, mixers, and detectors for microliter to nanoliter quantities of gases, liquids, and solids. Also, optical waveguide probes and ultrasonic flexural-wave sensors can now be produced on a microscale. The integration of these microfabricated devices into a single systems allows for the batch production of microscale reactor-based analytical instruments. Such integrated microinstruments may be applied to biochemical, inorganic, or organic chemical reactions to perform biomedical and environmental diagnostics, as well as biotechnological processing and detection.

The operation of such integrated microinstruments is easily automated, and since the analysis can be performed in situ, contamination is very low. Because of the inherently small sizes of such devices, the heating and cooling can be extremely rapid. These devices have very low power requirement and can be powered by batteries or by electromagnetic, capacitive, inductive or optical coupling.

The small volumes and high surface-area to volume ratios of microfabricated reaction instruments provide a high level of control of the parameters of a reaction. Heaters may produce temperature cycling or ramping; while sonochemical and sonophysical changes in conformational structures may be produced by ultrasound transducers; and polymerizations may be generated by incident optical radiation.

Synthesis reactions, and especially synthesis chain reactions such as the polymerase chain reaction (PCR), are particularly well-suited for microfabrication reaction instruments. PCR can selectively amplify a single molecule of DNA (or RNA) of an organism by a factor of $10^6$ to $10^9$. This well-established procedure requires the repetition of heating (denaturing) and cooling (annealing) cycles in the presence of an original DNA target molecule, specific DNA primers, deoxynucleotide triphosphates, and DNA polymerase enzymes and cofactors. Each cycle produces a doubling of the target DNA sequence, leading to an exponential accumulation of the target sequence.

The PCR procedure involves: 1) processing of the sample to release target DNA molecules into a crude extract; 2) addition of an aqueous solution containing enzymes, buffers deoxyribonucleotide triphosphates (dNTPS), and oligonucleotide primers; 3) thermal cycling of the reaction mixture between two or three temperatures (e.g., 90–96, 72, and 37–55° C.); and 4) detection of amplified DNA. Intermediate steps, such as purification of the reaction products and the incorporation of surface-bending primers, for example, may be incorporated in the PCR procedure.

A problem with standard PCR laboratory techniques is that the PCR reactions may be contaminated or inhibited by the introduction of a single contaminant molecule of extraneous DNA, such as those from previous experiments, or other contaminants, during transfers of reagents from one vessel to another. Also, PCR reaction volumes used in standard laboratory techniques are typically on the order of 50 microliters. A thermal cycle typically consists of four stages: heating a sample to a first temperature, maintaining the sample at the first temperature, cooling the sample to a second lower temperature, and maintaining the temperature at that lower temperature. Typically, each of these four stages of a thermal cycle requires about one minute, and thus to complete forty cycles, for example, is about three hours. Thus, due to the large volume typically used in standard laboratory procedures, the time involved, as well as the contamination possibilities during transfers of reagents from one vessel to another, there is clearly a need for microinstruments capable of carrying out the PCR procedure.

Recently, the cycling time for performing the PCR reaction has been reduced by performing the PCR reaction in capillary tubes and using a forced air heater to heat the tubes. Also, an integrated microfabricated reactor has been recently developed for in situ chemical reactions, which is especially advantageous for biochemical reactions which require high-precision thermal cycling, particularly DNA-based manipulations such as PCR, since the small dimensions of microinstrumentation promote rapid cycling times.

This microfabricated reactor is described and claimed in copending U.S. application Ser. No. 07/938,106, filed Aug. 31, 1992, entitled "Microfabricated Reactor", assigned to the same assignee. Also, an optically heated and optically interrograted micro-reaction chamber, which can be utilized, for example, in the integrated microfabricated reactor of the above-referenced copending application Ser. No. 07/938, 106, has been developed for use in chemical reactors, and is described and claimed in copending U.S. application Ser. No. 08/489,819, filed Jun. 13, 1995, entitled Diode Laser Heated Micro-Reaction Chamber With Sample Detection Means", assigned to the same assignee.

The present invention is directed to a particular geometry of silicon-based and non-silicon-based micro-reactors that have shown to be very efficient in terms of power and temperature uniformity. The micro-reactor of this invention, which is broadly considered as a silicon-based or non-silicon-based sleeve device for chemical reactions, can be effectively utilized in either of the reactor systems of the above-referenced copending applications. The present invention utilizes, for example, doped polysilicon for heating and bulk silicon for convective cooling. The present invention allows the multi-parameter, simultaneous changing of detection window size, in situ detection, reaction volumes, thermal uniformity, and heating and cooling rates. In addition, it enables the use of large arrays of the individual reaction chambers for a high-throughput microreaction unit.

SUMMARY OF THE INVENTION

It is an object of the present invention to provide an improved chemical reaction chamber.

A further object of the invention is to provide a silicon-based or non-silicon-based sleeve type chemical reactor.

A further object of the invention is to provide a microfabricated reactor that uses a combination of materials.

A further object of the invention is to provide a chemical reaction chamber that combines to use of doped polysilicon and bulk silicon.

A further object of the invention is to provide a microfabricated chemical reactor having a sleeve reaction chamber with a slot therein for introducing reaction fluids, either directly or via a tube.

A further object of the invention is to provide silicon or non-silicon reaction sleeves that combines critical ratios of materials to provide the proper thermal characteristics.

A further object of the invention is to provide silicon or non-silicon reaction sleeves that combine a critical ratio of materials to provide control of reagents and products.

A further object of the invention is to provide silicon or non-silicon reactions sleeves that combine a critical ratio of materials to provide the proper thermal response.

A further object of the invention is to provide chemical reaction chambers that combines, for example, the use of doped polysilicon and bulk silicon to provide flexibility in thermal and optical properties allowing the implementation into small and large instruments.

Another object of the invention is to provide an interconnected series or array of silicon or non-silicon reaction sleeves thereby providing a flow-through reaction system.

Another object of the invention is to provide a silicon-based reaction sleeve that combines a critical ratio of silicon and silicon nitride to the volume of material to be heated (e.g., liquid) in order to provide uniform heating, yet low power requirement.

Another object of the invention is to provide a sleeve reaction chamber that will allow the introduction of an insert (e.g., plastic) into the reaction sleeve that contains the reaction mixture, thereby eleviating any potential materials incompatibility issues.

Another object of the invention is to provide an interconnected series or array of silicon or non-silicon reaction sleeves connected by tubing of polymers, metals, glasses, and ceramics, similar to a "string of beads" in appearance.

Another object of the invention is to provide an array of individual reaction chambers for a high-throughput microreaction unit.

Another object of the invention is to provide a hand-held instrument that uses sleeve-type reaction chambers with integrated heaters.

Another object of the invention is to provide a reaction chamber with automated detection and feedback control.

Another object of the invention is to provide for artificial intelligence control of reactions in a reaction chamber.

Another object of the invention is to provide pulse-width modulation as a feedback control for reaction chamber.

Another object of the invention is to provide reaction control with magnetic films, thermoelectric films, or electroactive films, such as electrodes.

Another object of the invention is to provide a combination of detection modules, such as electrochemiluminescence, optical, electrical and capacitive.

Another object of the invention is to provide a combined reaction chamber with microelectrophoresis channels.

Another object of the invention is to provide, a reaction chamber made from silicon and non-silicon directly coupled with microelectrophoresis channel made of silicon or non-silicon.

Another object of the invention is to provide a sleeve-type reaction chamber with microelectrophoresis channel coupled via an internal liner.

Another object of the invention is to provide a microelectrophoresis detection system based on optical, electrical, or magnetic devices.

Another object of the invention is to provide a microelectrophoresis detection system based on light emitting diodes and photodiodes.

Other objects and advantages of the present invention will become apparent from the following description and the accompanying drawings. Basically, the invention is a silicon-based or non-silicon-based sleeve for chemical reactions. The invention encompasses a chemical reaction chamber that combines, for example, the use of polysilicon for heating and bulk silicon for convective cooling. The reaction chamber may combine a critical ratio of non-silicon and silicon based materials to provide the thermal properties desired. The silicon-based reaction sleeve, for example, may combine a critical ratio of silicon and silicon nitride to the volume of material to be heated in order to provide uniform heating, yet low power requirements. The reaction sleeve of this invention also allows for the introduction therein of a secondary tube or insert that contains the reaction mixture thereby eleviating any potential materially incompatibility issues. The present invention is an extension of the above-referenced integrated microfabricated reactor of above-referenced copending application Ser. No. 07/938,106 and the above-referenced optically integrated micro-reaction chamber of above-referenced copending application Ser. No. 08/489,819. The sleeve reaction chamber can be utilized in chemical reaction systems for synthesis or processing of organic, inorganic, or biochemical reactions, such as the polymerase chain reaction (PCR) and/or other DNA reactions (such as the ligose chain reaction), or other synthetic, thermal-cycling-based reactions.

BRIEF DESCRIPTION OF THE DRAWINGS

FIG. 21 illustrates an embodiment of a micromachined ECL cell with a thin film anode, and an associated photodiode detector.

FIG. 22 is an enlarged cross-sectional view of the ECL cell of FIG. 21 with the electrical leads.

FIG. 31 illustrates an embodiment using Al on ITO on glass which reduces resistance of the ITO electrode.

DETAILED DESCRIPTION OF THE INVENTION

The present invention is a micro-fabricated sleeve chemical reaction chamber. A silicon-based embodiment combines features such as doped polysilicon for heating and bulk silicon for conventive cooling, for example. The microreaction chambers, made of silicon-based or non-silicon-based materials can be used in an array for a high-throughput microreaction unit, or in a hand-held unit. The reaction chambers may combine critical ratios of non-silicon and silicon based materials to provide the thermal properties desired. The hereinafter described silicon-based embodiment combines, for example, a critical ratio of silicon and silicon nitride to the volume of material to be heated (e.g., liquid) in order to provide uniform heating, yet low power requirements. The invention also will allow the introduction of an insert or secondary tube (e.g., plastic) into the reaction sleeve that contains the reaction mixture thereby alleviating any potential materials incompatibility issues. The hereinafter described embodiment of the present invention utilizes a particular geometry of silicon-based micro-reactors that have been shown to be very efficient in terms of power and temperature uniformity. The particular embodiment of the microfabricated reactor described has been experimentally used as a thermal cycling instrument for use in the polymerase chain reaction (PCR) and other chemical reactions, and has shown to be superior to present commercial instruments on thermally-driven chemical reactors. The silicon-based or non-silicon-based sleeve reaction chamber of this invention can be utilized in place of the reaction chamber of the microfabricated system of above-referenced copending application Ser. No. 07/938,106; and can be utilized with the integrated heater and detection arrangement of above-referenced copending application Ser. No. 08/489,819, and thus constitutes an extension of the microfabricated chemical reaction systems in these copending applications.

To provide an understanding of a microfabricated chemical reaction instrument and the integrated heating/detection arrangement, prior to the description of the embodiment of the silicon-based sleeve reaction chamber made in accordance with the present invention, a description is set forth of a microfabricated chemical reactor and an integrated heating/detection arrangement of the two-referenced copending applications. While the sleeve reaction chamber is described hereinafter as being constructed of silicon-based materials, non-silicon-based material may be utilized for certain applications wherein the materials are compatible with the reaction fluids and/or are chemically inert.

Figure 1:
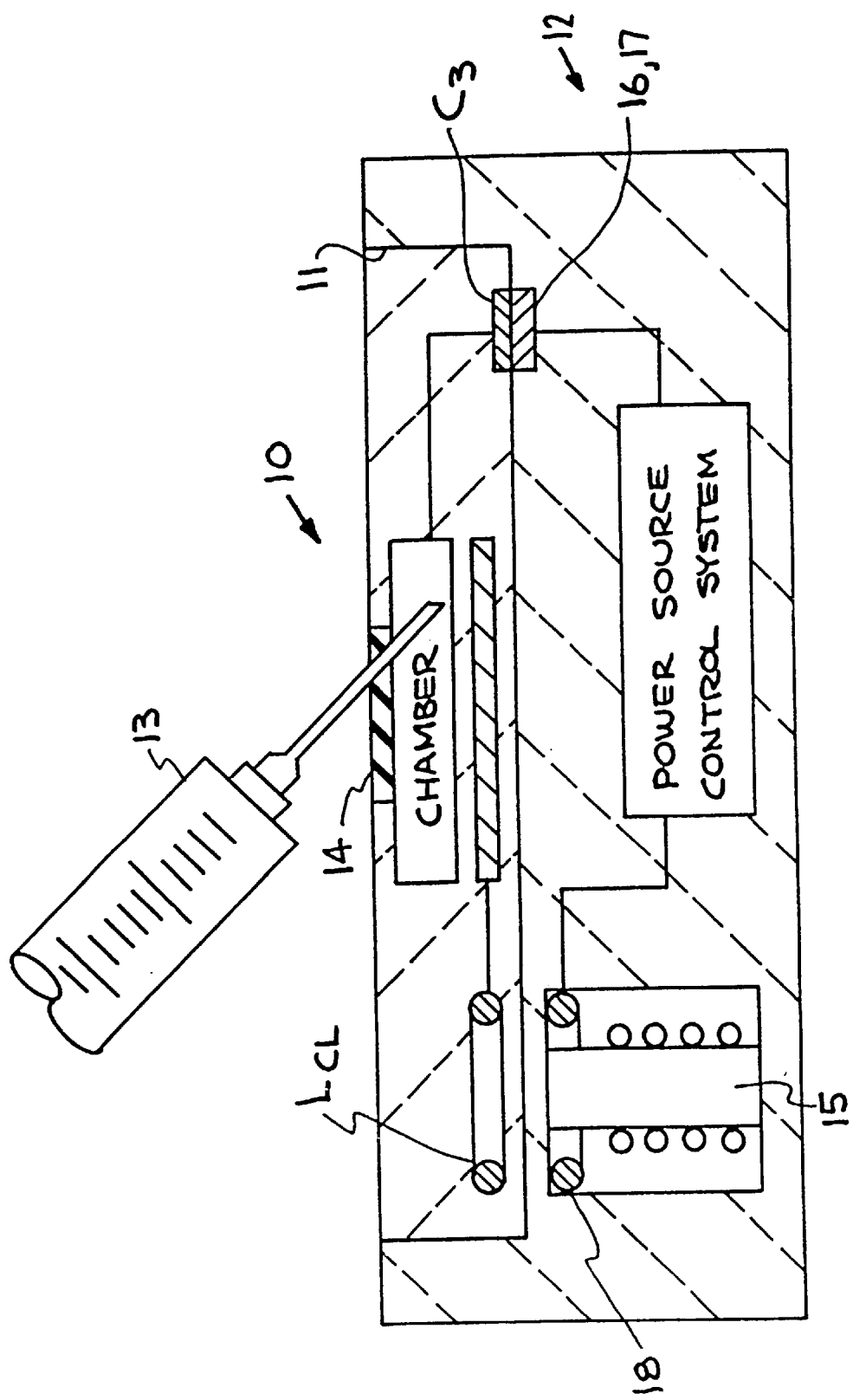
FIG. 1 shows a partial cut-away perspective view of a microfabricated chemical reaction instrument mounted in a power source/control apparatus.

FIG. 1 illustrates an embodiment of a microfabricated chemical reaction instrument generally indicated at 10, shown above a recessed section thereof, indicated generally at 11, in a power source/control system of the microfabricated reaction instrument, generally indicated at 12. A hypodermic needle 13 is shown inserting a sample through a silicone rubber window 14 into the reaction instrument 10. The reaction is controlled and powered by: induction coupling, such as that between coil $L_{CL}$ in the instrument 10 and a magnetic coil 15; by capacitive coupling, such as that between the plates of capacitor: $C_3$ and plates 16 and 17; and by electromagnetic coupling between a resonant circuit, see FIG. 2, in instrument 10 and a radio frequency antenna 18.

Figure 2:
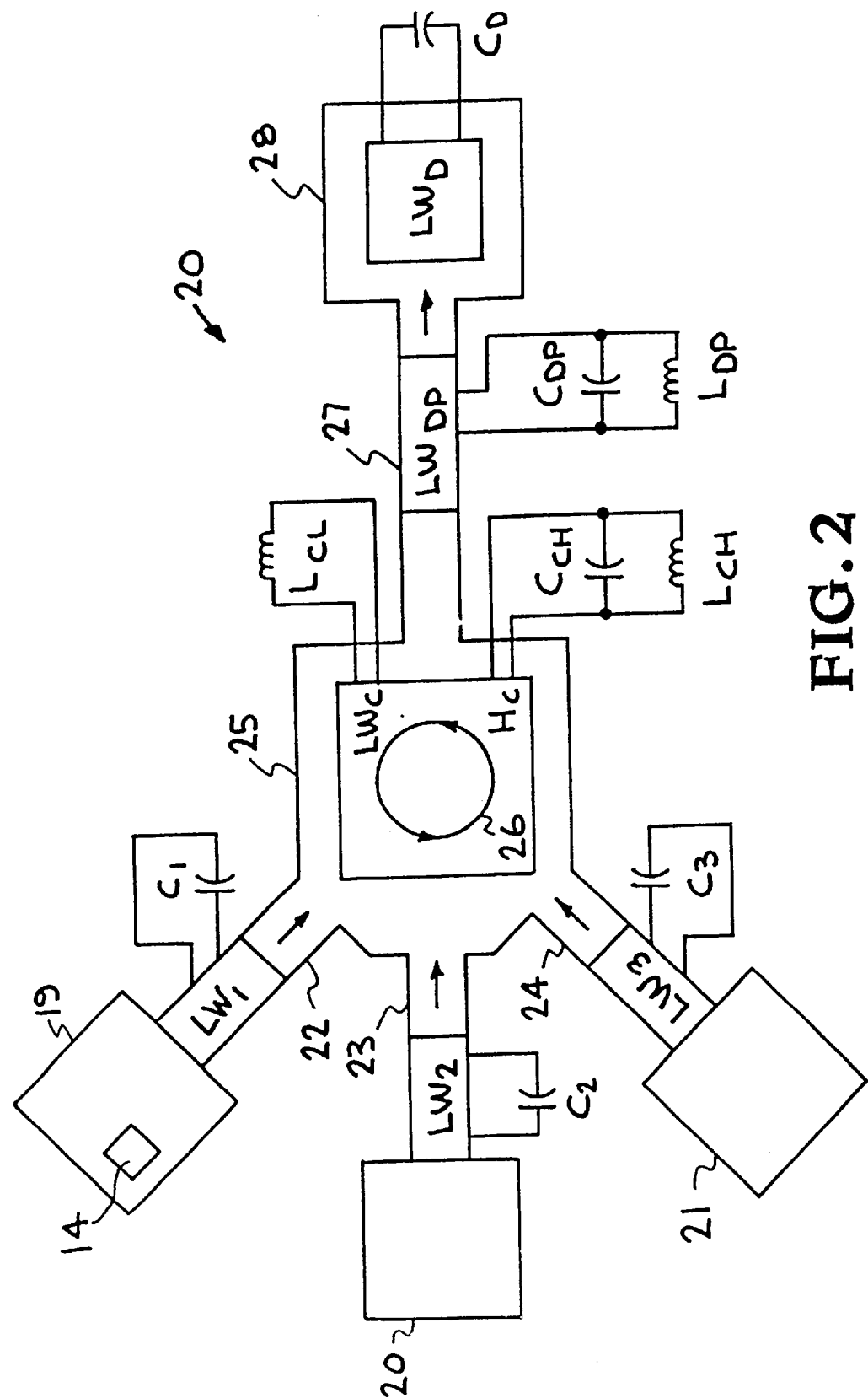
FIG. 2 is a schematic of the reaction instrument of FIG. 1.

A schematic of the instrument 10 of FIG. 1 is illustrated in FIG. 2, and comprises three reagent chambers 19, 20 and 21, which, for example, may contain the DNA primers, the polymerase, and the nucleotides and any detection-tag molecules, such as magnetic beads. The target DNA molecule is placed in reagent chamber 19 by insertion of a hypodermic needle 13 (FIG. 1) or the like through a silicone rubber or other type material window 14. The reactants chambers 19, 20 and 21 are respectively connected by channels 22, 23, and 24, having narrow midsections, not shown, to a reaction chamber 25. Typically the chambers 19–21 and 25 have a volume ranging from microliter to nanoliters. The channels 22–24 are equipped with Lamb-wave pumps $LW_1$, $LW_2$ and $LW_3$, respectively, for pumping reactants in chambers 19–21 through channels 22–24 in the direction of the arrows into reaction chamber 25. The Lamb-wave pumps may be located on any wall, or on multiple walls, of the channels 22–24. The Lamb-wave pumps $LW_1$, $LW_2$, and $LW_3$ are connected respectively to capacitors $C_1$, $C_2$, and $C_3$. The surface tension across the narrow midsections of the channels 22–24 prevents the reactants in chambers 19–21 from flowing into reaction chamber 25 until pumping is initiated. The inner surfaces of the channels 22–24 may be treated to raise the surface tension thereby further inhibiting flow of the reagents when the Lamb-wave pumps are not activated.

The reaction chamber 25 may be equipped with a Lamb-wave transducer $LW_C$ and a heater $H_C$. The Lamb-wave transducer $LW_C$ is connected to inductor $L_{CL}$ (also shown in FIG. 1). The heater $H_C$ is connected to a resonant circuit consisting of an inductor $L_{CH}$ and a capacitor $C_{CH}$. The Lamb-wave transducer $LW_C$ acts as an agitator, mixer, or sonochemical inducer, as indicated by the connected arrows 26 in chamber 25.

A channel 27 connects the reaction chamber 25 to a detection chamber 28. The channel 27 is equipped with a Lamb-wave pump $LW_{DP}$, which is connected to a resonant circuit consisting of an inductor $L_{DP}$ and a capacitor $C_{DP}$. The detection chamber 28 is equipped with a Lamb-wave sensor $LW_D$, which is connected to a capacitor $C_D$.

Lamb-wave transducers have high mechanical Q values and can therefore be powered by only a narrow range of alternating voltage frequencies. The Lamb-wave pumps ($LW_1$, $LW_2$, $LW_3$) and Lamb-wave sensor ($LW_D$) are powered capacitively by generating an electric field between the plates (such as plates 16 and 17 of FIG. 1 for example) at the resonant frequencies of the Lamb-wave transducers ($LW_1$, $LW_2$, $LW_3$, and $LW_D$). But, because the transducers have high Q values, only when the frequency of the imposed field is near the resonant frequency of a transducer do the transducer vibrate with any substantial magnitude. Similarly, the Lamb-wave mixing chamber transducer $LW_C$ is provided by an alternating frequency magnetic field generated by the coil (15 in FIG. 1) at the mechanical resonant frequency of the transducer $LW_C$. The heater $H_C$ and the Lamb-wave pump $LW_{DP}$ are activated by directing an electromagnetic wave from the antenna (18 in FIG. 1) to the resonant circuit $C_{CH}$ and $L_{CH}$, and resonant circuit $C_{DP}$ and $L_{DP}$, respectively. The frequency of the incident electromagnetic radiation must correspond to the mechanical resonant frequency of the transducer $LW_{DP}$, to activate the pump $LW_{DP}$. The frequency of the incident electromagnetic radiation must correspond to the resonant frequency of the electrical elements CH, $L_{CH}$ and $H_C$ to activate the heater $H_C$.

A PCR reaction, for example, is initiated by pumping the reagents in the chamber 19, 20 and 21 along the directions of the arrows through respective channels 22, 23 and 24 to the reaction chamber 25 by activating pump $LW_1$, $LW_2$, and $LW_3$. A series of about twenty to forty thermal cycles, for example, are then initiated, and during each cycle the temperature of the reactants in the reaction chamber 25 goes from 55° C. to 96° C., and back to 55° C., for example. The temperature of the reaction chamber 25 is determined by the power of the incident electromagnetic signal at the frequency corresponding to the resonant frequency of the circuit composed of the capacitor $C_{CH}$, and the inductor $L_{CH}$, together with the heater $H_C$. The Lamb-wave device $LW_C$ of the reaction chamber 25 acts as an agitator or mixer, as indicated by arrows 26, to mix the reagents and promote the reaction.

When the thermal cycling is complete, the contents of the reaction chamber 25 are pumped by the Lamb-wave perm $LW_{DP}$ through channel 27 in the direction of the arrow to the detection chamber 38, which utilizes a Lamb-wave sensor $LW_D$. Alternatively, the detection chamber 28 may be provided with an optical window and testing may be performed by fluorescence-based or absorption-based optical spectroscopy.

Figure 3:
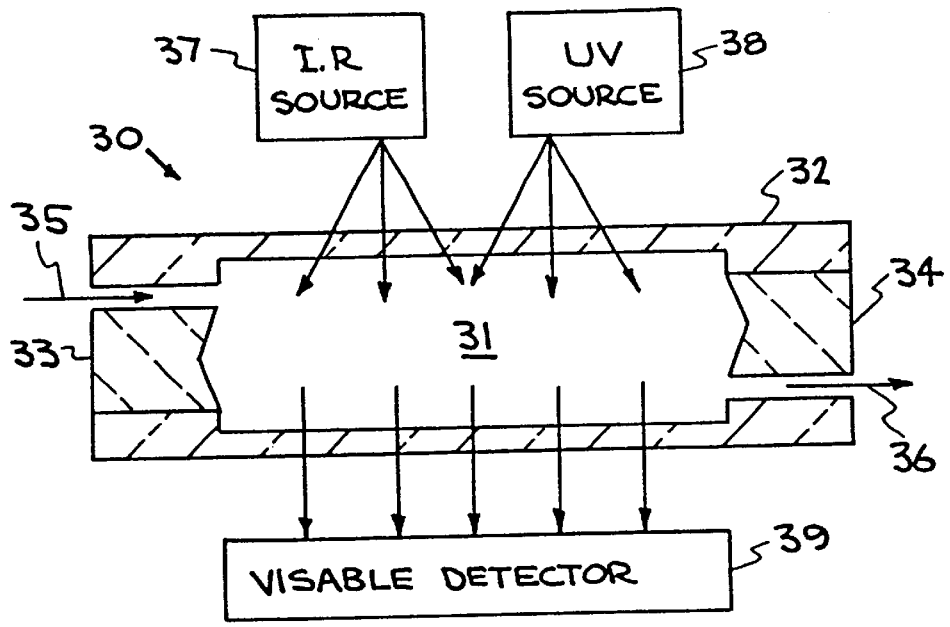
FIG. 3 schematically illustrates a heating and detection arrangement for a microfabricated reaction chamber.

FIG. 3 illustrates a heating/detection arrangement that can be incorporated into the microfabricated reactor of FIGS. 1 and 2. As shown in FIG. 3, a chemical reaction chamber, such as a PCR chamber, of a miniaturized, microfabricated instrument, generally indicated 30, is illustrated in cross-section, with chamber 31 being formed in a housing 32, constructed of Pyrex for example, and having silicon inserts 33 and 34 therein, with an inlet 35 and an outlet 36. Energy from two different energy (light) sources is directed onto the housing 32, one source 37 being infrared (IR) source, and the second source 38 being an ultra-violet (UV) source. The IR source 17 applies heat more uniformly through the bulk of the solution in chamber 31. The UV source 18 induces fluorescence of the reaction products in the visible (Vis) spectrum, which can be detected by a visible (Vis) detector 39 located external of the housing 32 defining reaction chamber 31. Housing 32 must be constructed of a material transparent to UV and/or the visible spectrum. By incorporating an integrated excitation (heating) and detection system in the reaction chamber itself, confirmation of the presence of a sample in the reaction chamber can be confirmed, and the dual reaction and detection chambers 25 and 28 of the microfabricated reactor of FIG. 2 can be consolidated, thus reducing fabrication costs by reducing components.

The present invention, an embodiment of which is illustrated generally in FIGS. 4 and 5 involves a microfabricated reactor generally indicated at 40 which includes a silicon-based sleeve as a chemical reaction chamber, generally indicated at 41, constructed of two bonded silicon parts, and which utilizes doped polysilicon for heating and bulk silicon for convective cooling, as described in greater detail hereinafter. The sleeve 41 includes a slot or opening 42 into which reaction fluid, indicated at 43, from a hypodermic needle 44 is inserted into the reaction chamber, or into which a secondary tube 45 containing a reaction mixture 46 may be inserted. The tube 45 is constructed of plastic, for example, or other material which is inert with respect to the reaction mixture, thereby alleviating any potential material incompatibility issues. The sleeve is also provided with an opening 47 in which is located an optical window 48, made, for example, of silicon nitride, silicon dioxide, or polymers. The silicon sleeve reaction chamber 41 includes doped polysilicon for heating and bulk silicon for convective cooling, and combines a critical ratio of silicon and silicon nitride to the volume of material to be heated (e.g., liquid) in order to provide uniform heating, yet low power requirements.

Figure 4:
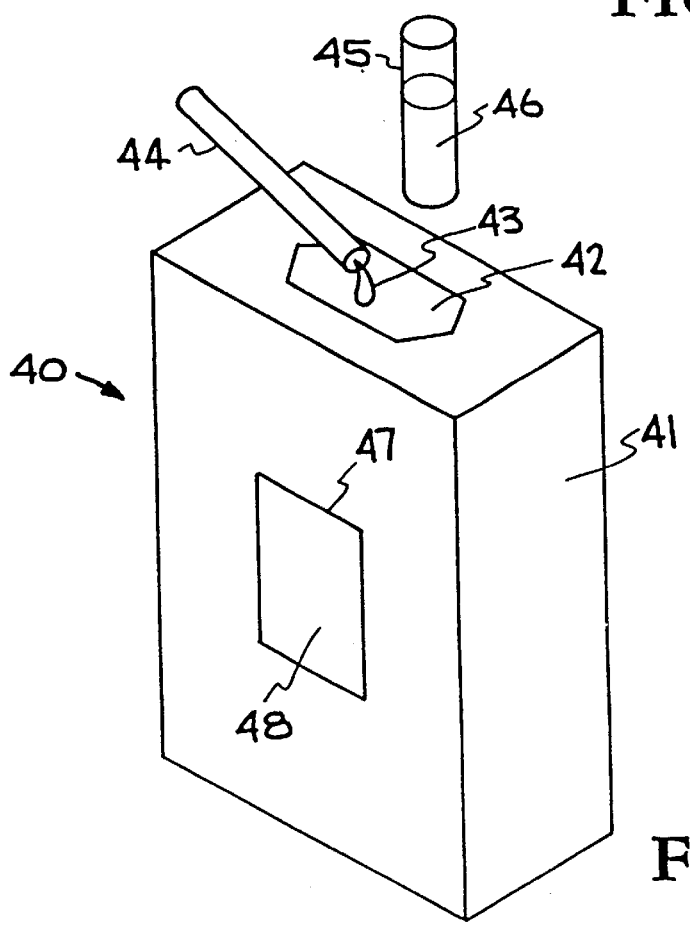
FIG. 4 illustrates an embodiment of a microfabricated silicon-based sleeve reaction chamber made in accordance with the present invention.
Figure 6:
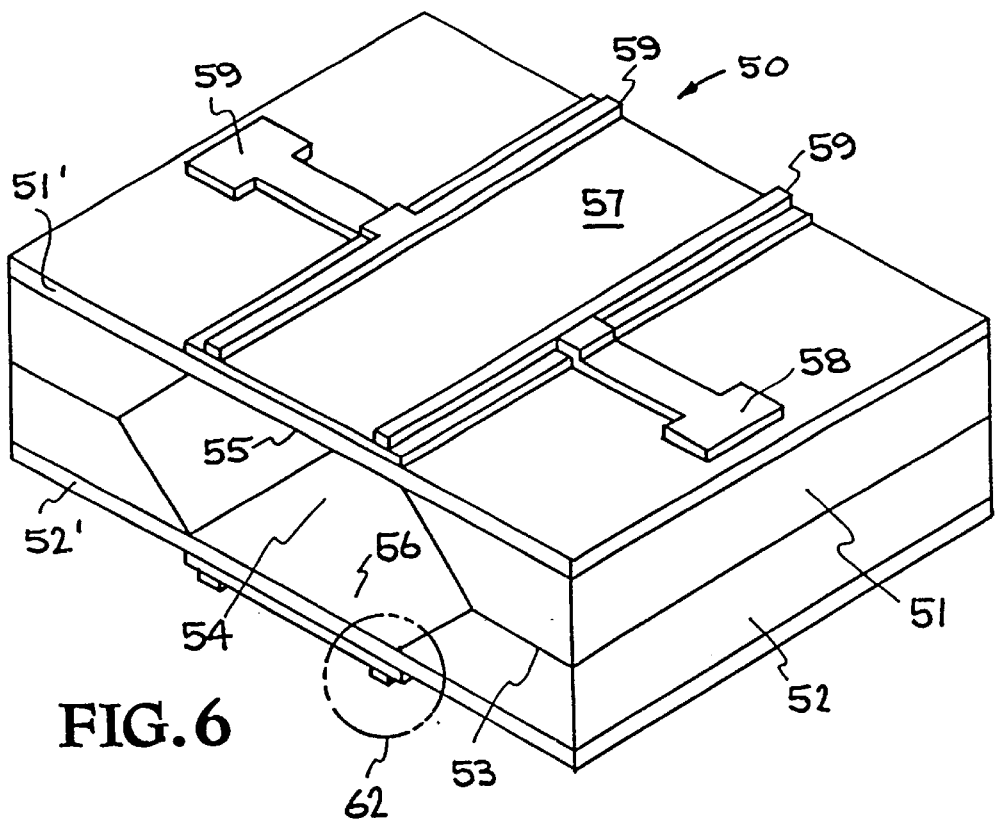
FIG. 6 is an enlarged end view of another embodiment of a sleeve microreaction chamber similar to FIG. 4.

FIG. 6 is an enlarged view of microreaction chamber, similar to the FIG. 4 embodiment, but utilizing two windows. The reaction chamber of FIG. 6, generally indicated at 50, is composed of two silicon wafers or substrates 51 and 52 bonded together as indicated at 53, and configured to define a slot or opening 54 therein. Each of wafers 51 and 52 include a layer of silicon nitride 51' and 52' which define a window, indicated generally at 55 and 56, respectively. Window 55 in wafer 51, constructed of silicon nitride, is provided with a heater 57 having electrical leads 58 and contacts 59 which extend along the edges of heater 57 to provide uniform heating. Window 56 in wafer 52 has a heater not shown in FIG. 6 but which is secured by metal contacts 60 and 61 as illustrated in either of FIGS. 7 and 8. The silicon nitride layers 51' and 52' are very thin (about 1 $\mu$m) and vapor-deposited onto the bulk silicon wafers 51 and 52. The silicon nitride only becomes a window, as indicated at 55 and 56, when the bulk silicon wafers 51 and 52 are etched away to form the opening or slot 54. Heater 57 is transparent to energy passing through window 55, for example.

Figure 7:
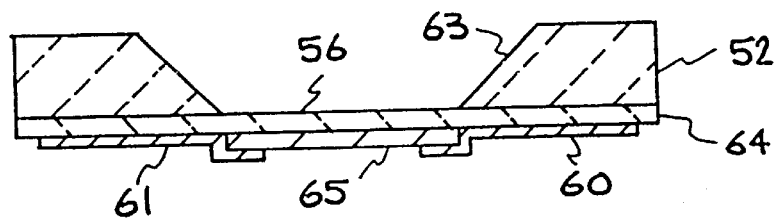
FIG. 7 illustrates in cross-section embodiment of an enlarged section of FIG. 6 using an isolated heater version, fixed window.

FIG. 7 is a greatly enlarged view of an embodiment of a section of silicon wafer 52 and window 56, as indicated by the circle 62 in FIG. 6. As seen in FIG. 7, the section of the silicon wafer 52, indicated at 63, is composed of bulk or single crystal silicon and is in contact with a low (100 to 500 MPa) stress silicon nitride membrane or window 64 (52' in FIG. 6) which in turn is in contact with a doped polysilicon heater 65 and metal contact 60 and 61. The FIG. 7 embodiment comprises an isolated heater version fixed window.

Figure 8:
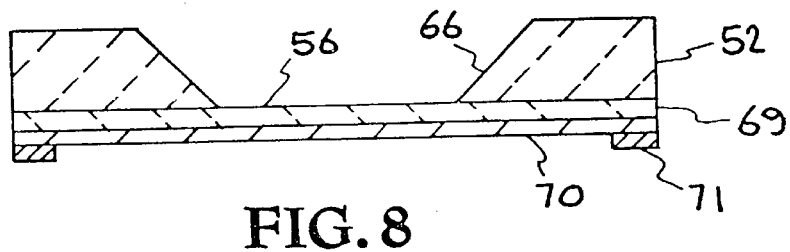
FIG. 8 illustrates in cross-section another embodiment of the same enlarged section of FIG. 6 using a non-isolated heater version variable window.

FIG. 8 is a greatly enlarged view of another embodiment of a section of silicon wafer 52 and window 56, as indicated by the circle 62. As seen in FIG. 8, the sections of the silicon substrate 52, indicated at 66 are composed of bulk or single crystal silicon. As in the FIG. 7 embodiment, a low (100 to 500 MPa) stress silicon nitride member or window 69 (52' in FIG. 6) is in contact with silicon section 66, a doped polysilicon heater 70 is in contact with window membrane 69 and metal contacts 71 are mounted to heater 70. The FIG. 8 embodiment comprises a non-isolated heater version. The window size relative to the chamber can be varied to ensure thermal uniformity and optical access to the reaction chamber.

By way of example, the silicon wafers or substrates 51 and 52 may have a length of 5 to 50 mm, width of 2 to 10 mm, thickness of 0.1 to 1.0 mm, with the slot 54 having a cross-sectional area of 5 to 500 mm$^2$. Slot 54, which shown to be of a six-sided configuration, may be a round, oblong, square, rectangular, or other configuration. Windows 55 and 56 may have a length of 0.1 to 1 mm, width of 0.1 to 50 mm, thickness of 0.1 to 10 $\mu$m, and in addition to silicon nitride, may be composed of silicon dioxide, silicon, or polymers. The doped polysilicon heater 65 of FIG. 7 may have a thickness of 0.05 to 5 $\mu$m, with the heater 70 of FIG. 8 having a thickness of 0.05 to 5 $\mu$m. The metal contacts 60–61 and 61' of FIGS. 6 and 7 may be composed of gold or aluminum, with a thickness of 0.01 to 5 $\mu$m, with the metal contact 71 of Figure having a thickness of 0.01 to 5 $\mu$m and composed of gold or aluminum. The heater 57 in silicon wafer or substrate 51 is composed of doped polysilicon having a thickness of 0.05 to 5 $\mu$m, with the electrical leads and contacts 58 and 59 being composed of gold or aluminum.

The use of bulk silicon, polysilicon, silicon nitride enables flexibility in design for thermal and optical properties of each chamber. This enables individually controlled, thermally isolated reaction chambers in a small instrument (FIG. 9) or in large instrument (FIG. 10).

Figure 9:
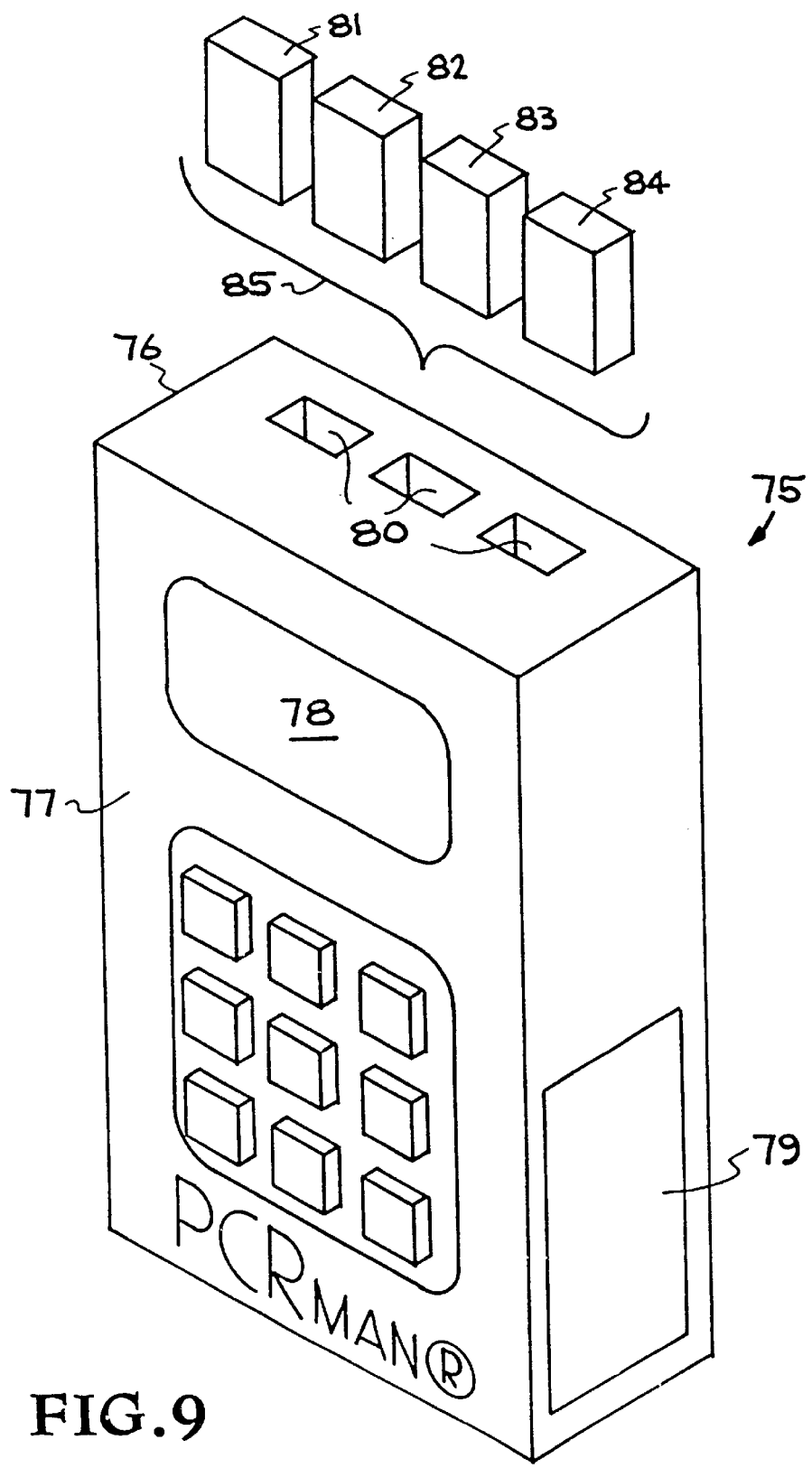
FIG. 9 is a view of a hand-held instrument (PCR man) which utilizes the reaction chambers of FIG. 6 as inserts to change reactions.

FIG. 9 is an embodiment of a miniature thermal cycling, battery operated, hand-held low-power, feedback-controlled instrument for PCR that uses microfabricated, silicon-based reaction chambers, such as those of FIGS. 4 and 6, the development of which addressed thermal uniformity and temperature precision of the reaction chambers, temperature ramp rates of the chambers, and biocompatibility of the materials in contact with the reagents.

As shown in FIG. 9, the hand-held, battery-operated instrument, coined "PCR man", generally indicated at 75, comprises a pressure-fit electrical contact controller holder, or housing 76, which for example may be 3×5 inches having a control-face-plate 77 with various indicators thereon, including a "status" window 78. The holder 76 is provided with a thermocouple-based temperature feedback control circuitry, heater electronics, computer interface, and power source connector, as described in greater detail hereinafter. The holder 76 is provided with batteries, indicated at 79, such as four nine-volt batteries, and at the upper end is provided with slots 80 for insertion of reaction chambers inside the holder (three slots shown), and into which silicon-based reaction chambers 81, 82, 83 and 84, with integrated heaters (as shown in FIG. 6) are inserted as indicated by the arrow 85. The reaction chambers 81–84 may when constructed contain different reagents or, chemicals, and can be selectively inserted into the hand-held instrument 75 via slots 80 in holder or controller 76.

This instrument can be used to rapidly and repetitively provide controlled thermal cycles to the reaction mixture. The thermal conductivity properties of the silicon or similar semiconducting substrate, for example, help speed up the thermal rise and fall times, and allow low power operation. While silicon is unique in its thermal properties, i.e., high thermal conductivity, a combination of silicon, silicon nitride, silicon dioxide, polymers and other materials would provide a combination of thermal conductivity and insulation that would allow thermal uniformity and low power operation.

While silicon or silicon-based materials is preferable, other materials can be used, including: polymers, ceramics (crystalline and non-crystalline, silicate and non-silicate-based), metals or combination of metals (alloys), composites, and a combination of materials (such as composite polymers that contain dopants (for example, aluminum oxide) that increase thermal conductivity, for example) in order to achieve the desired thermal properties (conductivity, resistance, specific heat, expansion, etc.), thermal mass, or other sensing and control capabilities. The compatibility of such materials need to be considered as well, especially in regards to its surface reactivity or inertness. The materials should also be selected based upon the ability or capability to integrate control elements onto or adjacent to them. In the case where liners are used, the chemical compatibility of less importance, but other features such as conductivity, etc., may still be of critical importance.

For example, it is possible to make a reaction chamber out of the proper thermal material (highly conductive) such as silicon or metal (i.e., copper) which may be noncompatible with the reaction, and use a chemical vapor deposition or evaporation process to deposit an ultra-thin polymer passivation layer (such as teflon or polypropylene) on the walls to achieve a compatible surface that is minimally compromised in terms of thermal conductivity.

It is the use of such microfabrication technologies that allows for such unique capabilities. Without them it would be difficult to fabricate reaction chambers with optimal reaction-control capabilities. Thin film processes and vapor deposition, for example, allows for extremely thin and uniform coatings of materials onto other materials, while etching and batch-fabrication allow for mass production.

Integration of control elements onto this variety of materials, which may include deposition (or other microfabrication method), is now possible in one form or another. For example, thin film metal heaters can be deposited onto polymer or ceramic devices, as can electrodes, sensing elements, circuits, etc.. The formation of IC-type electronics and control elements can be deposited onto many of the materials available today. The selection of the materials and microfabrication method only needs to be based on the needs of the application, since a wide variety of options exist. Reaction chambers are a prime example of an application that benefits from this breadth of availability. The heating and/or cooling means for the reaction chamber may be composed of thermo electric film, for example.

Integration of microfabricated magnetically-active films, for example, with the reaction chambers or series of reaction chambers can be used to control reaction reagents and products. This can be accomplished by the use of magnetic or paramagnetic particles in the reaction fluid that are capable of selectively binding to specified reagents. Through the use of the magnetic attraction and repulsion forces that can be created between the film and the particles, the desired reagents could be selectively attracted or repulsed, while the retaining reagents could be carried away via the flow-through system.

The incorporation of microfabricated thermoelectric films or heaters, as another example, could be used to control the temperature of the reactions in the sleeve-type reaction chambers. Both heating and cooling can be accomplished with such films allowing the reagents to experience elevated and below ambient thermal regimes. Series of temperature or mechanically actuated pressure zones will generate fluid flow conditions for directed throughput.

Other active micromachined films or devices can be incorporated to affect the reaction rate, mixing, flow or transport within the system. Examples include microfabricated actuators such as shape memory films (i.e., NiTiCu), electrostatic actuators such as polyimide, thermal bimorph actuators such as polyimides or other materials with different thermal expansion coefficients, and other micromachined structures.

The particular embodiment, such as FIG. 6, of a microfabricated reactor described can be used as a thermal cycling instrumentation for use in the PCR and other chemical reactions, biochemical processes, microbiological processes, and incubators. As shown hereinafter the reaction chamber of this invention is superior to present commercial instruments used in thermally-driven chemical reactions.

During the experimental verification of the instrument of FIG. 9 and the microreaction chambers for use therein, such as illustrated in FIGS. 4 and 6, several different sizes of PCR reaction chamber designs were fabricated using integrated circuit (IC)-type silicon processing steps. The generalized fabrication process was as follows: Three-inch round, 0.5 mm thick single crystal silicon (SCS) wafers were processed in the following way: low stress (200–300 MPa) silicon nitride ($Si_xN_y$) was low-pressure chemical vapor (LPCVD) deposited onto entire wafer (1.0–2.0 $\mu$m thick). Photolithographic patterns for reaction chamber and subsequent processing steps were taken in the following order: 1) the silicon nitride was reactive ion etched (RIE) over the reaction chamber area, 2) the SCS was etched to the silicon nitride backside defining the chamber volume, 3) the wafer was patterned and the silicon nitride is chemically etched away everywhere except over the nitride membrane or left over the entire surface, depending upon the reaction chamber design, 4) the remaining silicon nitride membrane (side opposite the chamber) was LPCVD deposited with polycrystalline silicon polysilicon) to a thickness of 3000 Å, 5) the polysilicon was then high temperature doped with boron to a resistivity of 50–200 ohms per square, and 6) either aluminum or gold thin-film metal contacts were deposited defining the heater geometry.

Each wafer potentially contains many reaction chambers, depending upon geometry and volume desired. The etched depression in each wafer constitutes one-half of a dual-heater reaction chamber. Processed wafers are subsequently bound together forming an enclosed chamber with heaters on both sides.

The reaction chambers can be bonded together by depositing a thin film of low-temperature-curing polyimide between the two wafers directly or other bonding techniques such as eutectic metal bonding. A high precision computer-controlled silicon saw was used in each design to cut out each dual-heater chamber. The chambers were then rinsed repeatedly with de-ionized water and dried prior to treatment with silane.

The reaction chambers were inserted into a pressure-fit electrical contact holder that was part of the plexiglass backboard of the electronics components making up the controller. The controller electronics could be either/or analog or digital and could use processes such as pulse-width modulation as a feedback control mechanism. The backboard was 3 inches by 5 inches and consisted of the thermocouple-based temperature feedback control circuitry, heater electronics, computer interface, and power source connector. The circuitry was designed to work from 8 to 32 volts. Thermal calibration was accomplished by correlating the temperature of the fluid with that of the silicon-measuring Type K thermocouple. Once calibrated, the instrument was capable of automated, feedback-controlled, thermal cycling operation without direct measurement of the reaction fluid. The thermal cycler output is to an Apple Centris 650 computer which displays the thermal cycle real-time along with storing the accumulated profiles. Four nine-volt batteries were able to run the entire instrument continuously for over 2.5 hours.

Typical PCRs were set up as scaled-up master mixes, to assure uniformity between aliquots thermocycled under different conditions. Reagent amounts were based on those ideal for 50 ul reactions. In general, master mixes contained: 50 mM KCl, 10 mM Tris-HCl pH 8.3, 1.5–3.0 mM $MgCl_2$, 200 uM each deoxynucleotide, or 800 uM dNTP total, 0.5 uM each of two oligonucleotide primers, 25 units/ml AmpliTaq® DNA polymerase, and target template at a specified copy number per 50 ul reaction. Template for some of the β-globin PCRs was added as single strand DNA from a M13 bacteriophage done of a portion of the human β-globin gene.

CF template was human genomic, double stranded, DNA derived from a cultured cell lines, HL60, GM07460, or GM08345. Each reaction mixture was aliquoted from the same master mix and thermocycled in the instrument of the present invention and a Perkin-Elmer, GeneAmp® 9600 Thermal Cycler. Thermocycled reactions from both thermal cyclers were fractionated on 3% NuSeive, 1% Seakem agarose (FMC Corp.) using tris-borate buffer. The gels were stained with ethidium bromide and photographed under illumination with 302 nm UV light.

Although initially conceived as a single use, disposable reaction chamber, the robust nature and stable properties allowed for repeated use of the reaction chambers.

The (MEMS) based thermal cycling instrument of this invention has been tested with a variety of PCR systems, including viral, bacterial, and human genomic templates. As well, various changes in both the reaction chamber design and controller instrumentation have been implemented and evaluated. A controller output real-time display of a thermal cycle from microfabricated thermal cycler has been prepared and it has been shown that with 15 volts input (average 1.2 Watts) that heating rates of over 5° C./sec are attained. Cooling is slightly slower (2.5° C./sec.) mostly due to the fact that the reaction chamber is held inside a Plexiglas instrument board. Precision of +/−0.5° C. is maintained at the target temperatures. Higher heating and cooling rates have been achieved.

We have performed experiments that show the quantitative nature of the PCR process in both FIG. 9 and commercial instruments. These experiments consisted of removing 5 $\mu$L aliquots out of a 105 starting copies, $\beta$-globin PCR from both the instruments at 23, 25, 27, 29, and 31 cycles. These aliquots were subsequently run on an agarose electrophoresis gel. The results from both instruments are virtually identical. The same quantitative gel electrophoresis series results from the amplification of the 268-bp target of $\beta$-globin directly from human genomic (HL60) DNA were performed.

Multiplex PCR is considered to one of the most recent and analytically-powerful DNA amplification techniques. It requires precise and uniform temperature control within the reaction chamber. We have achieved this with the instrument of this invention.

Post-PCR-detectionof the specific mutations associated with the cystic fibrosis, (CF) disease, for example, can be identified with simple nylon-based test strips, using reverse-dot-blot technology. The test strip has specific, immobilized DNA probes containing the mutation sequence of interest. The multiplex PCR amplification products are put into a simple reagent trough along with the assay. If binding occurs and the DNA is retained after a wash step, the DNA-biotin-streptavidin-enzyme complex will turn color upon treatment with the substrate. The commercial and the FIG. 9 instrument-amplified results of PCR followed by reverse-dot-plot assay for CF prepared.

From the results of the above-referenced experiments and previous results, relative to the above-identified copending applications, with single-sided heaters, silicon-based reaction chambers of various sizes and configurations are capable of carrying out chemical reactions, such as PCR, with low power requirements.

The significance of the above-reference experimental results is that for the first time, battery-operated, hand-held, PCR amplification; and simple reagent-based, targeted detection of complex biologicals and diseases can be carried out in an instrument such as illustrated in FIG. 9.

Figure 11:
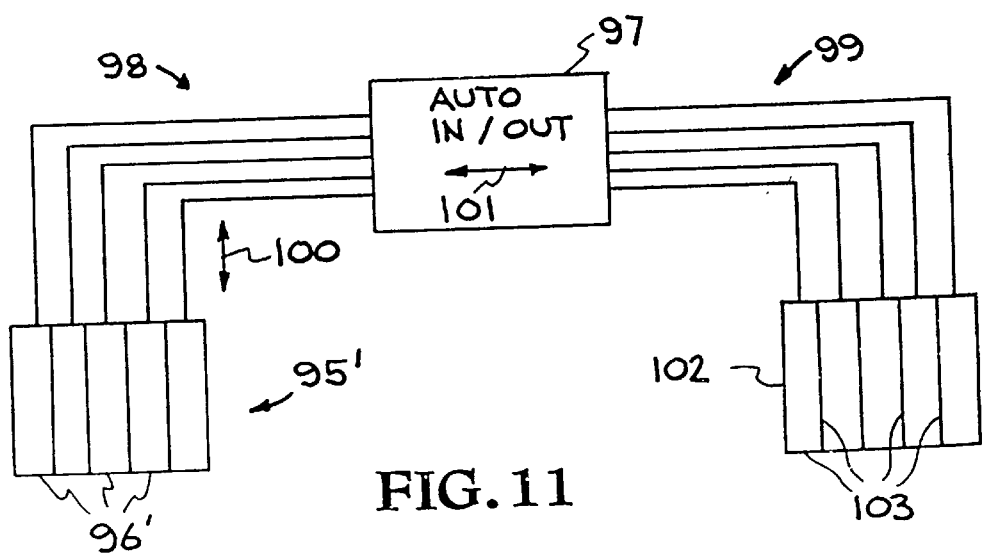
FIG. 11 illustrates a schematic representation of high-throughput DNA amplification, sample-handling, and electrophoresis system.
Figure 10A:
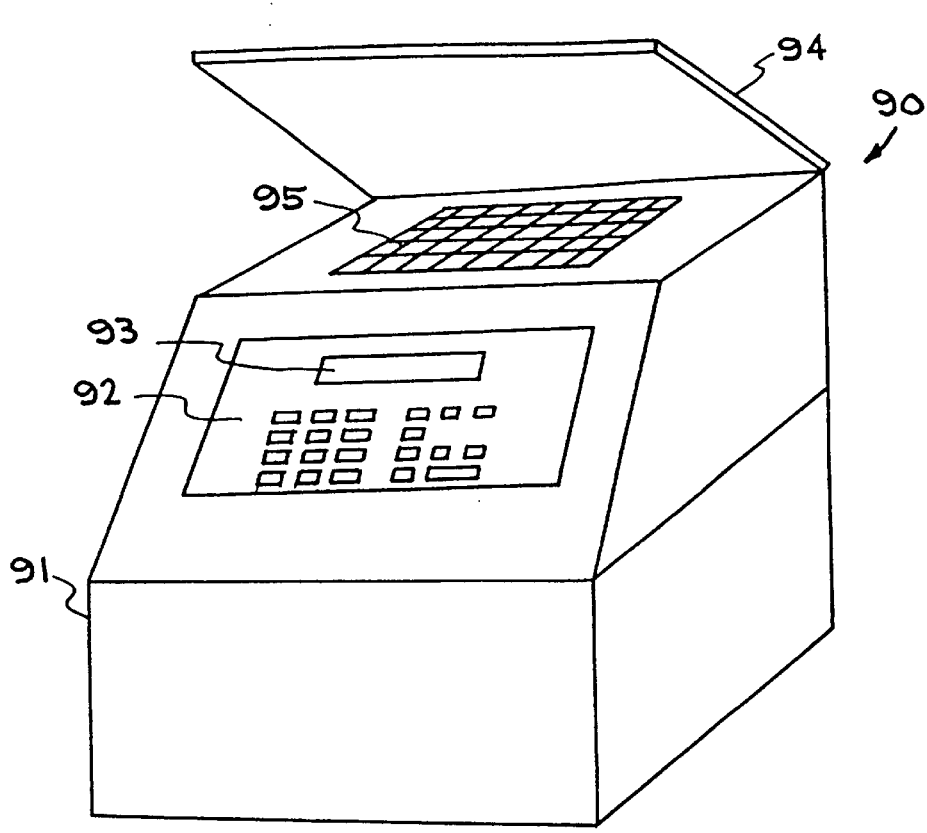
FIGS. 10A and 10B illustrate a thermal cycling instrument utilizing several hundreds of individually-controlled silicon-based microreaction chambers.
Figure 10B:
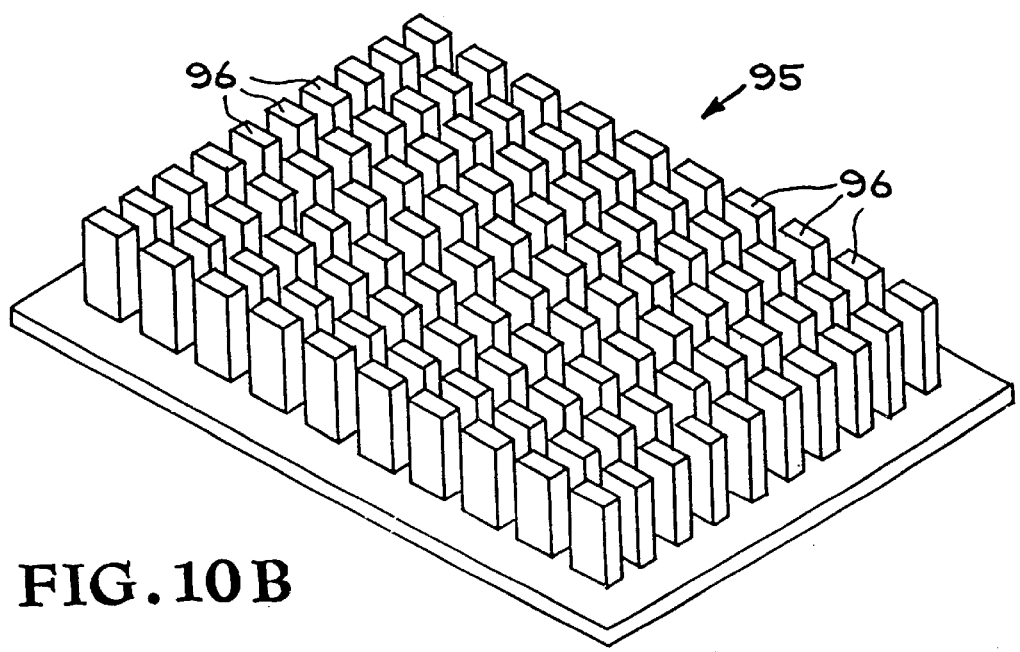

The rapid temperature cycling and thermal uniformity now possible in a PCR-type compatible silicon-based microreaction chamber may provide insight into hybridization and enzyme kinetics. For example, the importance of temperature control is paramount in the PCP process, especially when complex systems are to be amplified (e.g., human genomic DNA, multiplex amplifications). Precise temperature control as well as thermal uniformity must be balanced. To truly miniaturize the instrument or take advantage of microfabricated reaction chambers in order to build a high-throughput instrumentation, such as illustrated in FIGS. 10A, 10B and 11, one must integrate the control elements on a unit-by-unit scale. Thermal properties of the various materials, used must also be balanced to combine efficient control with thermal liability. Silicon-based materials afford the requisite thermal properties, the ability to integrate heaters and feedback control, and their manufacture takes advantage of highly parallel, automated, and batched processing.

FIGS. 10A–10B and 11 illustrate a system approach, combining the high-throughput, high efficiency thermal cycler instrument, sample handling, and electrophoresis modul. The electrophoresis module could also be micromachined in glass or silicon. The instrument could be hybrid in nature; i.e., a silicon based reaction chamber and a mini glass electrophoresis module taking advantage of both substrates or members, as in the FIG. 5 embodiment. The advantage to having real-time detection of DNA production is that it allows the operator to know about the PCR efficiency during the reaction, rather than waiting to see the results on a gel. This will significantly help DNA sequencing productivity by eliminating time wasted running electrophoresis gels on samples that haven't amplified.

FIGS. 10A and 10B illustrate a thermal cycling instrument, generally indicated at 90, having a housing 91 with a face plate 92 with various indicators thereon, including a "status" window 93, similar to the faceplate of the FIG. 9 hand-held instrument. The housing includes a hinged top 94, under which is located an array 95 (see FIG. 10B) of individually controlled silicon-based microreaction chambers 96, which may, for example, be of the type illustrated in FIGS. 4 and 6. The instrument 90 is designed for 384 microreaction chambers 95, although the array 95 as shown in FIG. 10B only includes 100 chambers for simplicity of illustration.

FIG. 11 is a schematic representation of high-throughput DNA application, sample-handling, and electrosystem utilizing the instrument of FIGS. 10A–10B, and corresponding reference numeral indicate corresponding components. An array 95' of 384 individual-controlled PCR reaction chambers 96' (only five shown, is operatively connected to an automated sample input/output assembly, generally indicated at 97 using two sets of microinjectors, generally indicated at 98 and 99. The sample input/output function between microinjector set 98 of assembly 97 and array 95 is indicated by double arrow 100, while the function between the sets 98 land 99 of microinjectors is indicated by double arrow 101. The microinjector set 99 is operatively to an array 102 of individual microelectrophoresis channels 103. This injector input/output system will load reagent samples from the reaction chambers 96 with vacuum or electrokinetic power; automatically or robotically move to electrophoresis channels 103; and unload reagents via pressure or reversed field electrokinetic injection into those channels for electrophoretic separation. The electrophoresis module could be micromachined as well. Silicon is good for reaction chambers, glass for electrophoresis.

Figure 5:
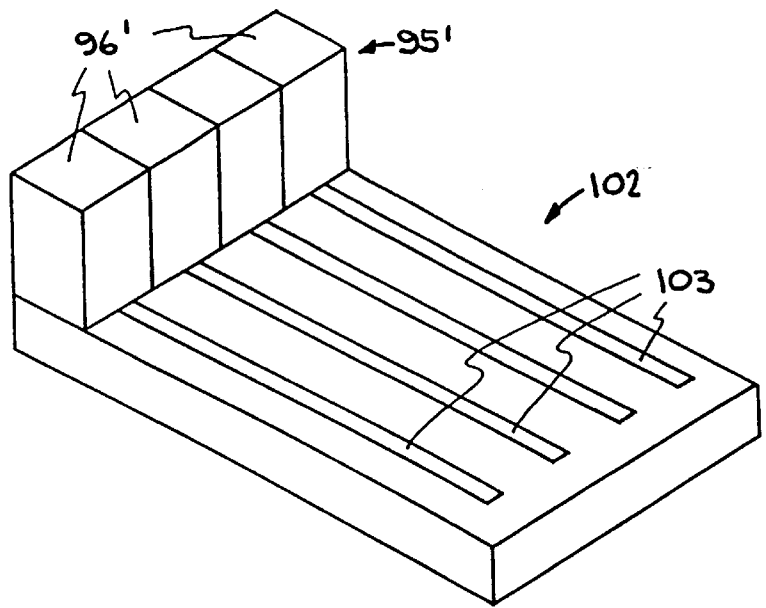
FIG. 5 is an array of the sleeve reaction chambers of FIG. 4 operatively connected to a microelectrophoresis array.

The electrophoresis channels 103, formed in a glass substrate are each directly connected to a silicon reaction chamber of the type shown in FIG. 4, so as to produce an array 95 of reaction chambers 96' connected directly to the array 102 of electrophoresis channels 103, as shown in FIG. 5.

By use of material in addition to silicon and silicon-based material described above with respect to FIGS. 5 and 11, the PCR/electrophoresis capability can be expanded. For example, the reaction chamber can be silicon, metal, ceramic as above for thermal considerations, the liner can be a polymer, glass, or other appropriate for compatibility and could have micromachined (CVD or evaporated) layers, and the electrophoresis channels could be glass, polymer, ceramic for electronic insulation or electronic in general considerations (this also could have CVD etc. deposited layers for compatibility and for control of electroosmotic flow or zetra potential). All the same concepts hold from above (i.e., IC-type integration of control elements. For example, a series of electrodes and optical detectors could be fabricated directly onto the substrate. The liner in that case actually directly interfaces to the electrophoresis microchannels.

Figure 12:
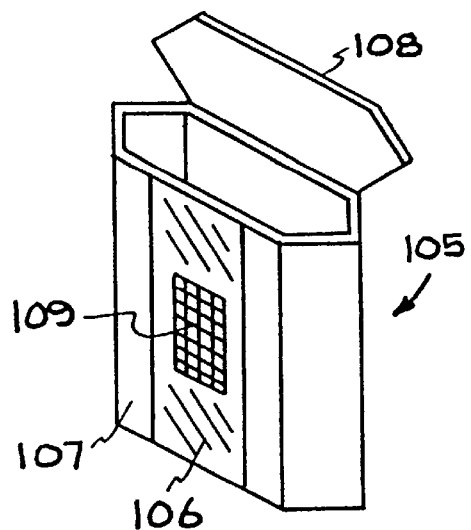
FIG. 12 is an embodiment of an insert/lining for a reaction chamber with optical window, with the top/cover open.

Removable/permanent lines/inserts for the reaction chambers of a material known to be compatible with the appropriate reactions, such as shown in FIG. 12 will in some applications reduce the overall cost, as these liners/inserts may be disposable. Also, considered are derivatizing agents for the surfaces of the silicon-based reaction chamber to enhance covalent and/or other bonding to the liners. Examples being the organic/reactive silanes, polyimides, teflons, polytheylene, other polymers.

FIG. 12 illustrates an embodiment of an insert/liner, generally indicated at 105, for a reaction chamber with an optical window 106 therein. The insert/liner 105 includes a six-sided housing 107 and a top/cover 108. The six-sided housing 107 is configured, for example, to be inserted into opening 54 of the reaction chamber 50 of the FIG. 6 embodiment, such that window 106 aligns with one of windows 55 or 56 of FIG. 6. The housing 107 may be constructed of plastic or other compatible material set forth above. Window 106 of insert/liner 105 includes a test strip 109, described hereinafter with respect to FIG. 14.

Figure 13:
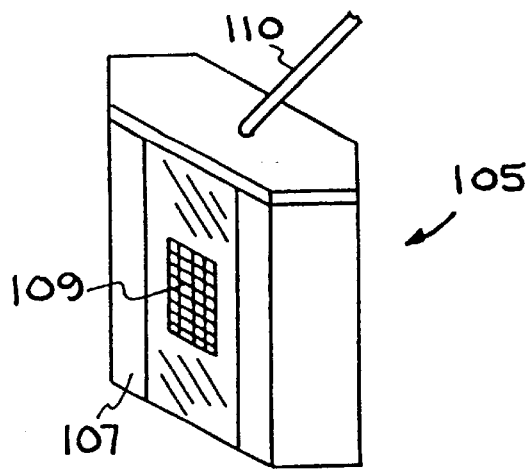
FIG. 13 illustrates external filling of a reaction chamber insert/liner.

FIG. 13 illustrates external filling of the reaction chamber insert/liner 105 of FIG. 12 via an external interfludic connection, generally indicated at 110. Examples of fluidic connections includes: syringe needles, pipette tips, and fused silica capillaries or glass or polymer tubing.

Figure 14:
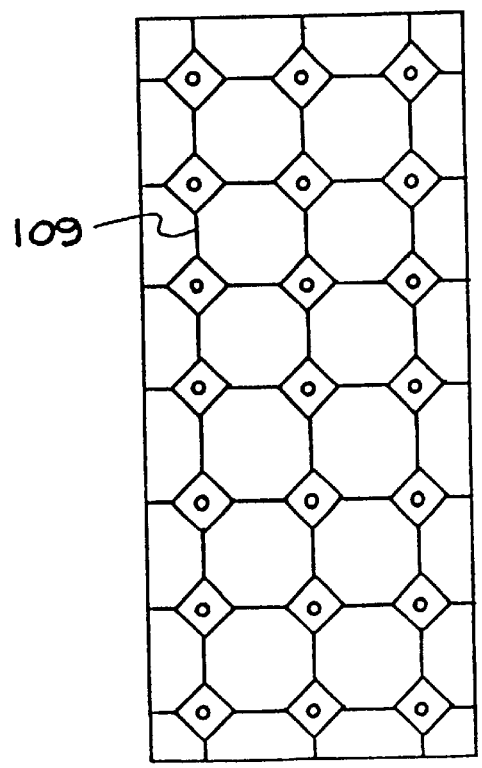
FIG. 14 illustrates immobilized reagents/probes for detection of specific products directly on windows or within reaction fluid a s "test strip" detected optically in the hand held instrument (PCR man) of FIG. 9.

Surface immobilization of the windows (or test strip) with probes for optical or other detection (other microbased detections) of product production and specificity, can be provided as shown in FIG. 14 which is an enlarged view of the test strip 109 of FIG. 12. Such a test strip can be included in the windows of the FIGS. 4 or 6 reaction chambers. Immobilized reagents/probes for detection of specific products directly on the window, such as 106 of FIG. 12, or within the reaction fluid in reaction chamber insert/liner 105 of FIG. 12, can be detected optically in the PCR man hand-held instrument of FIG. 9, by the use of the test strip 109. The actual inner surface of the window could be used as an immobilization surface for specific-target or product detecting probes, or the window could be used to view an immobilization/detection surface within the chamber.

Figure 15:
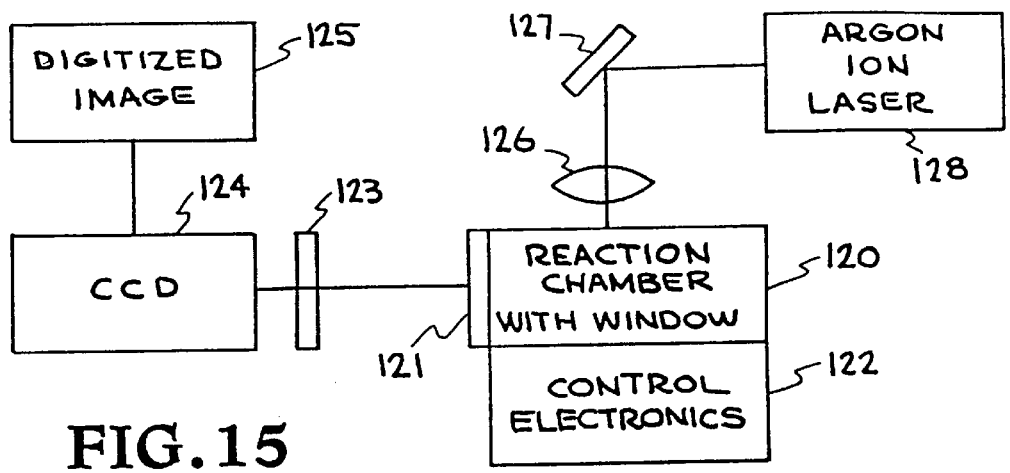
FIGS. 15 and 16 schematically illustrate optical detection systems for use with the microreaction chambers of FIG. 6.
Figure 16:
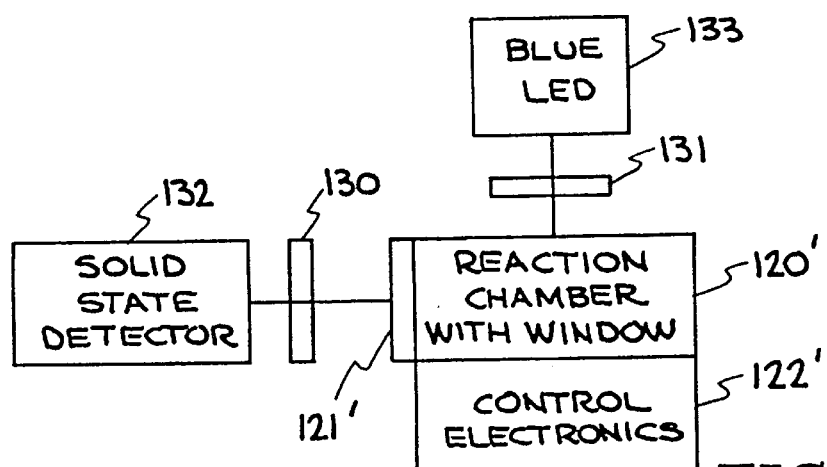

FIGS. 15 and 16 schematically illustrate two setups for optical detection. The FIG. 15 setup is a laser/ccd version, while the FIG. 16 setup will allow low-power operation for implementation into the PCR man (hand-held instrument) of FIG. 9.

As shown in FIG. 15, this optical detection arrangement for a reaction chamber 120 with a window 121 and control electronics 122, includes an optical filter 123, such as an interference filter or band pass filter for passing the detection wavelength of interest, CCD 124, digitized image generally indicated at 125, focusing optics 126, reflector/splitter 127 and an Argon ion laser 128. The operation is as follows: The laser excites the fluorescent indicator dye associated with product detection. The fluorescent signal is monitored by the CCD 124. Absorption spectroscopy could similarly be used.

FIG. 16 is a miniaturized optical detector system for reaction chamber 120' having a window 121' and control electronics 122' is composed of two filters 130 and 131, a solid state detector 132 and a Blue LED 133. The filters 130 and 131 are either band pass or long pass for selecting emission (i.e., 600 nm long pass) and band pass for selecting the excitation wavelength of interest, such as 488 nm±10 nm. The excitation band pass can be used to select from the typically broad emission of an LED, for example. The operation of the FIG. 16 detection system is as follows: The LED is filtered to 488±10 nm as an excitation source (or absorption) for the fluorescent indicating dye. The solid state detector is also filtered to receive only the wavelengths of detection (>600 nm) or as an absorption detector.

Figure 17:
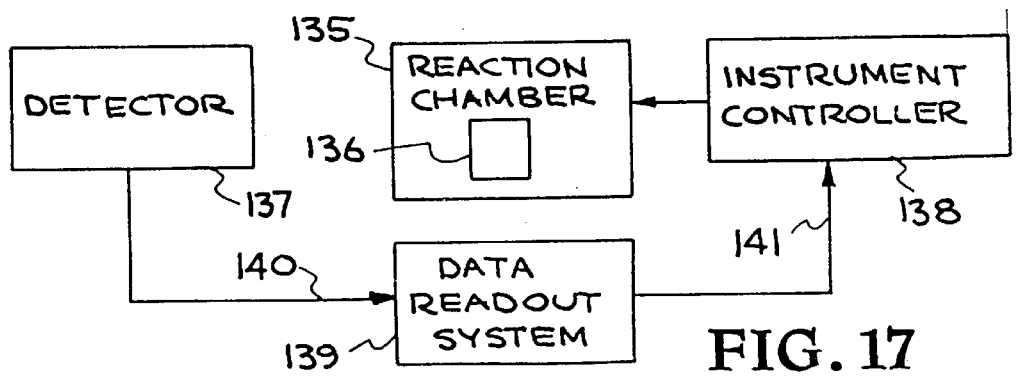
FIG. 17 schematically illustrates the use of integrated detection for an artificial intelligent feedback system.
Figure 18:
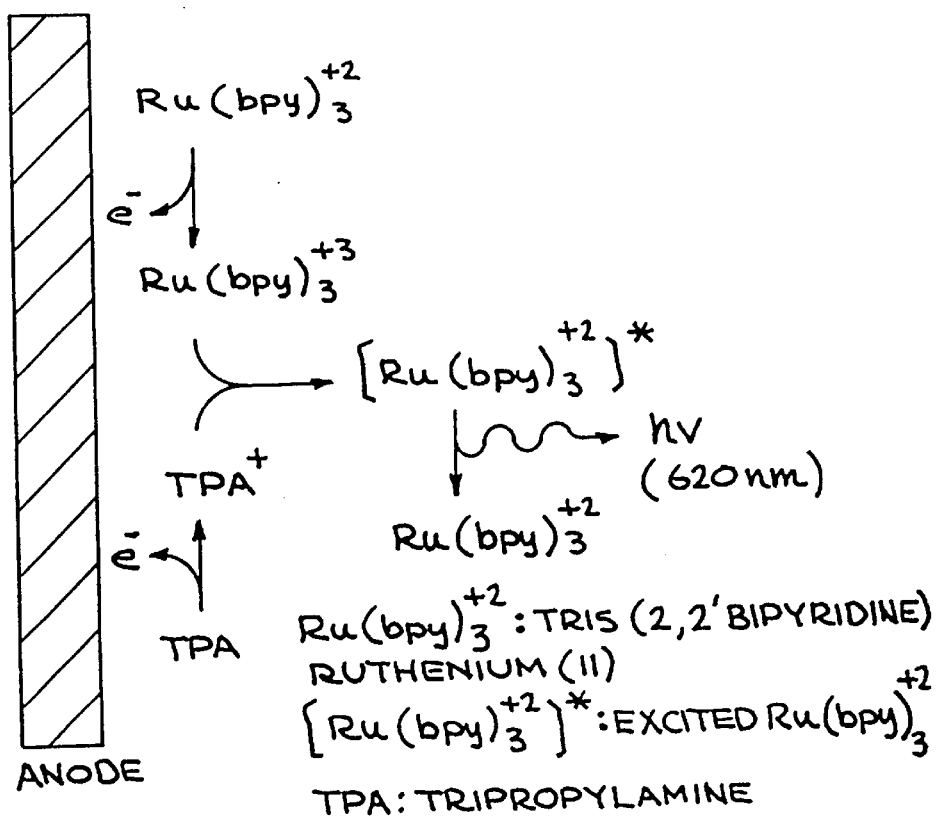
FIG. 18 is a diagram showing the electrochemical oxidation and chemical reduction reactions for tris(2,2'bipyridyl) ruthenium(II) (TBR) and tripropylamine (TPA).

Artificial intelligence is one way to produce DNA and determine how many cycles to go, when it is complete, if it worked, adjustment of parameters to improve production, etc. Using a real-time detection systems such as illustrated schematically in FIG. 17, an artificial intelligent feedback system using integrated detection can be provided. The system of FIG. 17 comprises a reaction chamber 135 having a window 136, a detector 137 for in situ detection of DNA production, an instrument control 138 for reaction chamber 135, and a data readout system 139, which receives data from detector 137, as indicated by arrow 140, and supplies control data to controller 138, as indicated by arrow 141. The data readout system 139 provides information such as how much DNA is being made, starting copy number, reaction complete, etc. By quantifying the DNA production via the optical monitoring system, which is well known, the system could adjust its cycling time and cycle number to produce the minimal number of cycles required for detection, thus speeding up the process. Also by determining the cycle number required to detect a given fluorescent signal, or product concentration, the system would be able to calculate all starting copy number or concentration of the unknown starting sample. This would allow automated concentration calculations. Real-time quantitative information can allow the system to adjust the reaction parameters such as target temperatures, hold times, and ramp rates.

A microfabricated, electrochemiluminesence cell for the detection of amplified DNA is described hereinafter with respect to FIGS. 18–31, and which sets forth the design, fabrication, and testing thereof. The microcell is designed to be the detection unit in a PCR micro-instrument, such as described above and illustrated in FIG. 9. The cell is a vertical assembly of micromachined silicon and glass and contains thin film electrodes, as shown in the Figures.

The detection of DNA by means of electrochemiluminescence starts with DNA amplification by PCR, to increase the concentration to detectable levels. Then it is labeled with tris(2,2'bipyridyl)ruthenium(II) (TBR). Oxidized TBR luminesces (orange) upon reduction. Oxidation occurs electrochemically at an electrode surface, hence the light emission is referred to as electrochemiluminescence (ECL). TBR requires a relatively low oxidation potential (a few volts) and has a high ECL efficiency in the visible (620 nm). This makes it attractive for microsensor applications, since visible emission is readily detected with silicon photodiodes, which could be integrated into a silicon micromachined cell. The reduction can occur electrochemically or chemically; in either case, light is emitted. For example, oxidized tripropylamine (TPA) readily transfers an electron to oxidized TBR, whereupon the TBR chemiluminesces. Since both oxidations can occur at the same electrode, relatively large concentrations of both species can be produced in close proximity, which results in higher light intensity for a given TBR concentration, than if TBR alone is present in solution. The electrochemical oxidation and chemical reduction reactions for TBR which occurs at the anode are schematically diagrammed in FIG. 18. Electrochemical reduction of TBR also occurs at the cathode. In order to oxidize only the TBR labeled DNA and not the free TBR, a separation of the two is required. One way to achieve this is by using the highly specific binding of immunoproteins (antibody-antigen).

Figure 19:
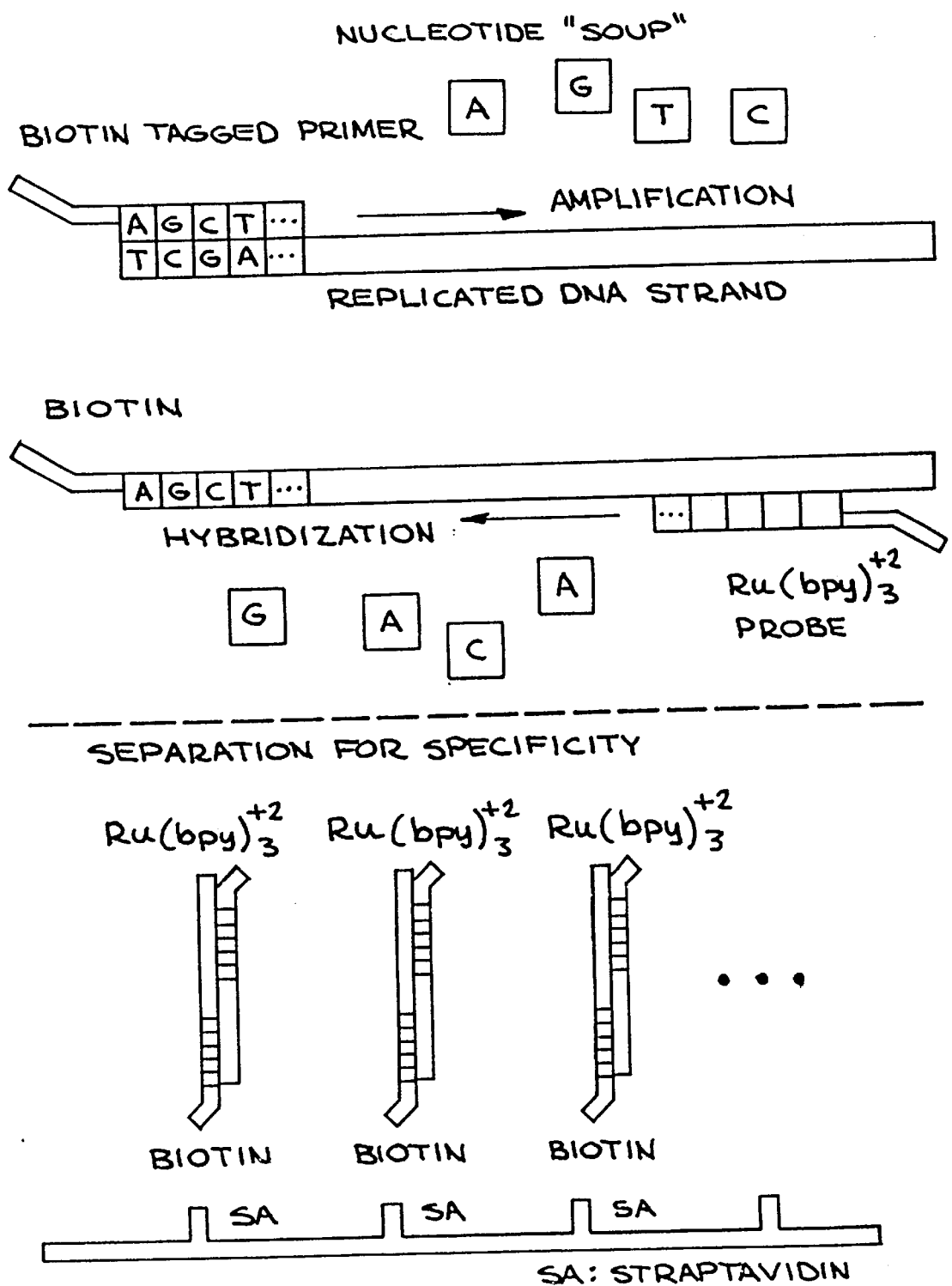
FIG. 19 illustrates a method for tagging and separating DNA for detection and quantification by electrochemiluminescence (ECL).
Figure 23:
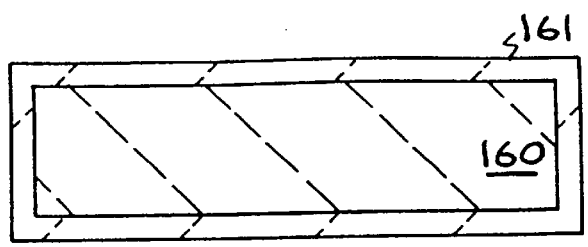
FIGS. 23–30 illustrate the fabrication process for producing an ECL cell, as illustrated in FIG. 21.
Figure 24:
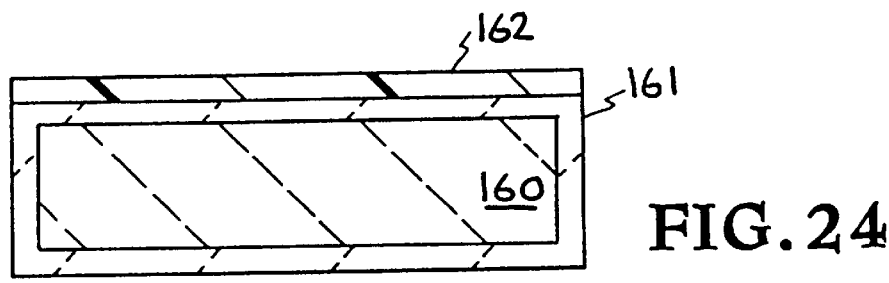
Figure 25:
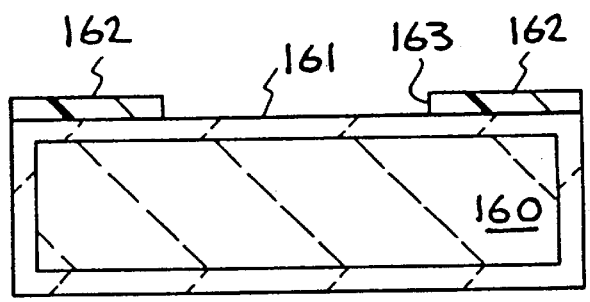
Figure 26:
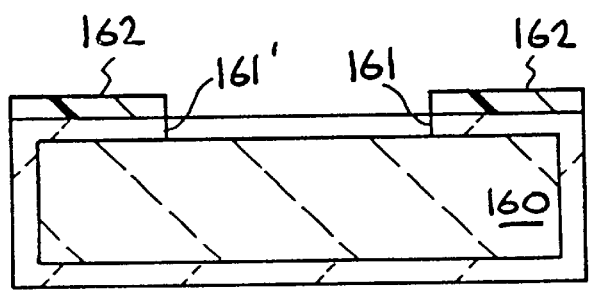
Figure 27:
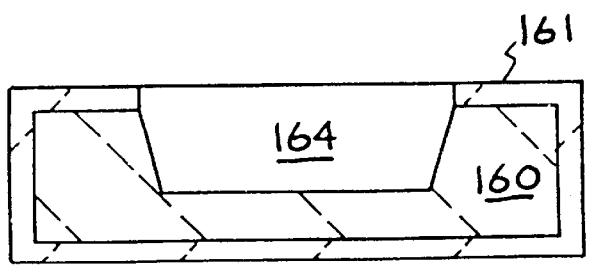
Figure 28:
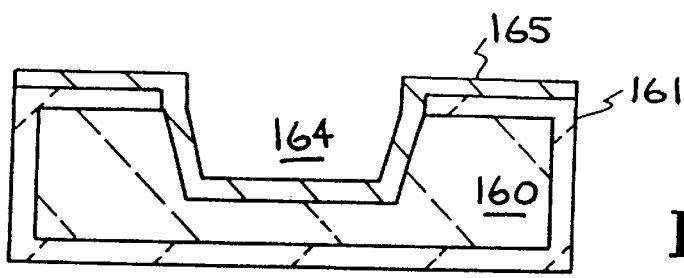
Figure 29:
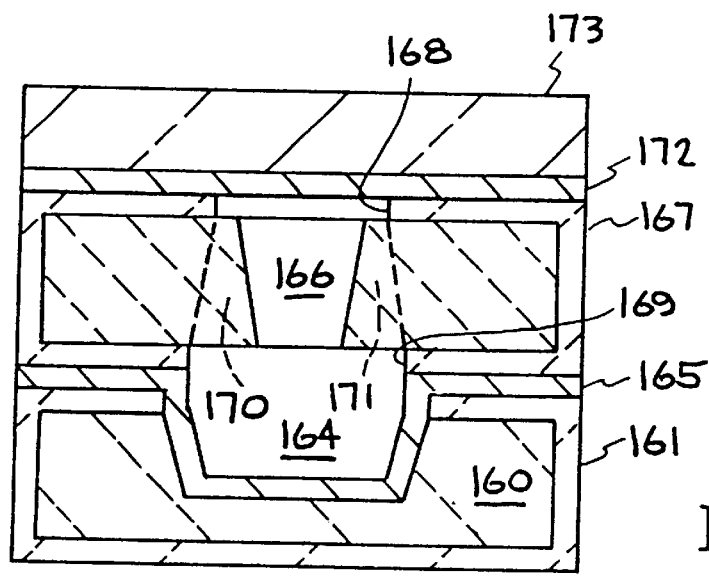
Figure 30:
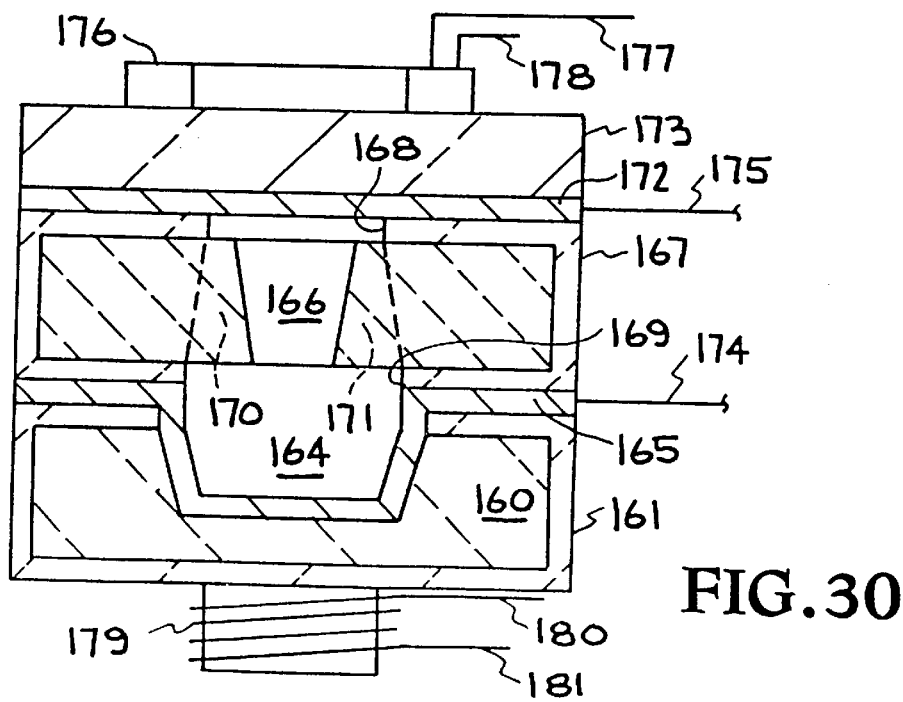

An example is shown in FIG. 19, where a biotin primer is made on a 5' end of one strand of target DNA and the TBR is tagged to the 5' end of the complementary strand. During the PCR process DNA double strands are produced with biotin and TBR labeled on either end. The biotin labeled DNA can then be introduced into an electrochemical cell with an anode whose surface is coated with avidin, the antibody for bioitin. Selective binding will occur, after which the solution in the cell is flushed to remove any "free" TBR. Now the TBR, bound to the DNA, which in turn is attached to the anode via the antibody-antigen bond, can be oxidized along with added TPA, and the subsequent luminescence intensity will depend on the amount of DNA that is present.

The ECL microcell, as described in greater detail hereinafter with respect to FIGS. 21–31, is a multilayer assembly of micromachined silicon and glass. Cells with solution capacity ranging from 35 $\mu$L to 85 $\mu$L have been designed and fabricated in silicon. An e-beam deposited, gold, thin film forms the cell cathode. The anode is also a thin film. Experiments with both indium tin oxide (ITO) and platinum have been carried out. ITO is transparent to visible light, so that when deposited onto glass, it can form the top layer of the assembly, through which the emitted light can be picked up by a photodetector (see FIG. 21). The assembly also contains micromachined fluid fill ports (see FIG. 22). The layers were assembled and bonded together (see FIGS. 29–30) using a low temperature curing polyimide, such as Epotek 400.

Figure 20:
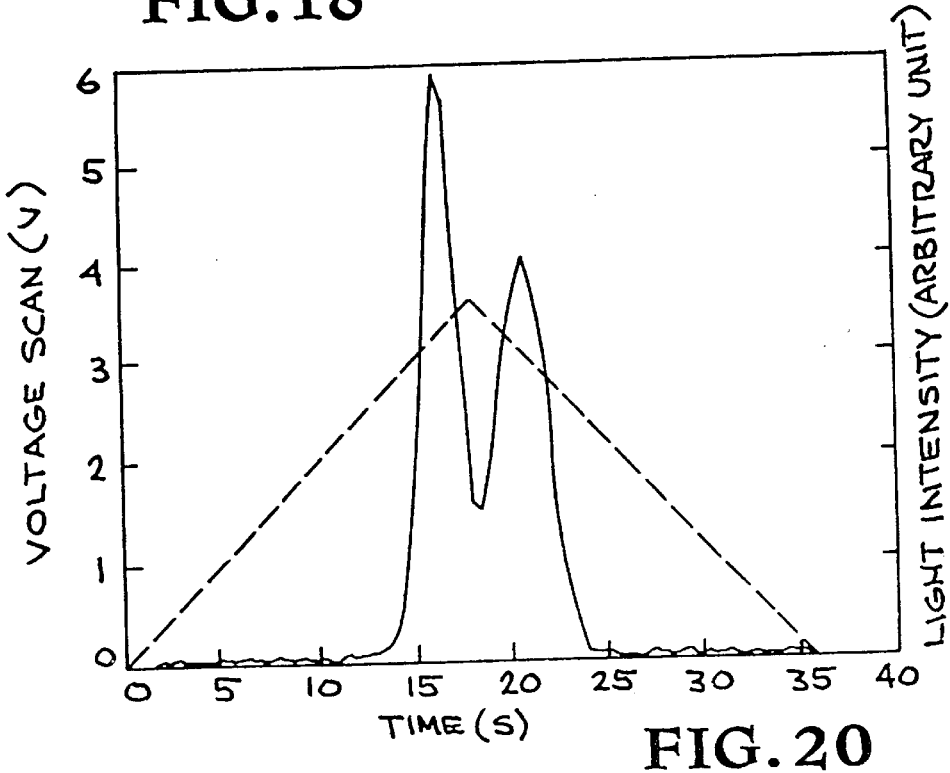
FIG. 20 illustrates cell voltage and ECL intensity versus time, with the voltage being increased, then decreased.

ECL experiments have been performed in the microcell with free TBR, i.e., no DNA. The cells were filled with TPA+TBR solution and a photomultiplier tube (PMT) was placed in close proximity to the top glass layer of the cell to detect emission. The chemiluminescence produced by the reaction of oxidized TPA and TBR depends on the concentration of both chemicals. In these experiments, the concentration of TPA was kept constant (50 mM) and TBR was varied. The solutions were prepared as follows: 1 g of TBR hexahydrate chloride was dissolved in 50 mM TPA to make 5 mM of TBR, which was then diluted with additional 50 mM TPA to produce a set of test solutions, whose TBR concentrations range from 0.1 nM to 5 mM. An EG&G potentiostat, model PARC 273, was used to produce voltammograms of the TBR+TPA solution, both in the microcell with ITO and gold thin film electrodes, and in a more conventional, electrochemical cell with platinum wire electrodes. From the voltammogram, the oxidation potential, which is where ECL occurs, was determined and then applied as a dc bias between the thin film cathode and anode. The emitted light was measured with a Hamamatsu MT, model R928, biased at 600 volt. FIG. 20 shows the relationship between measured light intensity and electrode voltage for a TBR concentration of /mM, where cell voltage and ECL intensity versus time. The voltage, as indicated by the dot-dash-dot line, is increased, then decreased. In both directions, the voltage passes through the oxidation potential of TBR, where intensity of ECL is a maximum. In tests conducted thus far, the lowest concentration of TBR that has been measured using the microcell with an ITO film as the anode material was 1 $\mu$M. With a platinum anode, the measured TBP concentrations were as low as 1 nM. The relatively high resistance of the ITO film is believed to be limiting the oxidation current for TPA, and therefore reducing the sensitivity. It has been determined that sensitivity can be improved by depositing a thin film of material, such as aluminum on the ITO film, as described hereinafter with respect to FIG. 31. Also, efforts are being carried out to integrate the silicon photodiode into the microcell, rather than being separated therefrom as in the FIG. 21 embodiment.

FIG. 21 illustrates an embodiment of a micromachined ECL cell with thin film anode, generally indicated at 140, and a silicon (Si) photodiode 141 positioned adjacent the ECL cell 140. The ECL cell 140 is shown in enlarged cross-section in FIG. 22. The cell 140 comprises a pair of silicon members 142 and 143, between which is positioned an electrode 144, which may be constructed of gold (Au), platinum (Pt) or silver (Ag), an ITO layer 145, and a glass layer or slide 146. Silicon member 142 includes a reaction chamber 147, and member 143 includes a pair of filling ports 148 (see FIG. 22) via which an analyte, as indicated by legend is directed into chamber 147 and withdrawn therefrom via tubes or lines 149 and 150, as indicated by arrows 151 and 152. As seen in FIG. 22, a center section 153 of silicon member 143 located between fill ports 148, along with ITO layer 145 and glass slide 146 define a window by which reactions within chamber 147 can be detected, as indicated by photons 154 passing therethrough onto photodiode 141. Electrical leads 155 and 156 are connected from a power source to electrode 144 and ITO layer 145, respectively, while photodiode 141 is electrically connected to a power source via leads 157 and 158.

FIGS. 23–30 illustrate the fabrication of an embodiment of an ECL cell similar to that of FIGS. 21 and 22. The fabrication process is carried out as follows:

1. A block 160 of silicon is coated to form a layer 161 of silicon nitride (see FIG. 23).
2. A layer 162 of photoresist is deposited on the layer 161 (see FIG. 24).
3. The layer 162 is patterned and photolithographic process to form an opening 163 therein (see FIG. 25).
4. The section 161' of silicon nitride layer 161 beneath the opening 163 is removed by RIE etching (see FIG. 26).
5. A section of silicon block 160 is removed by KOH etching to form a reaction chamber 164, and the remaining photoresist 162 is removed (see FIG. 27).
6. A layer of gold, for example, is deposited by thin film evaporation over the upper surface of block 160 and chamber 164 to form an electrode 165 (see FIG. 28).
7. A second block of silicon 166 is coated with a layer 167 of silicon nitride and openings 168 and 169 are formed therein by RIE etching, and a pair of filling ports 170 and 171 are formed, as by micromachining, in block, 166, and silicon nitride coated block 166 is bonded to electrode 165 (see FIG. 29).
8. A layer of ITO forming an electrode 172 is deposited on a layer or slide 173 of glass, and then bonded to the silicon nitride layer 167 (see FIG. 29).

9. Electrical leads 174 and 175 are secured to gold electrode 165 and ITO electrode 172, a detector 176, such as the photodiode of FIG. 21, having electrical leads 177 and 178 is bonded to glass layer 173, and the silicon nitride coated silicon block 160 is positioned on a magnet 179 having electrical leads 180 and 181 (see FIG. 30).

To reduce resistance of the ITO electrode 172 a thin film of aluminum 182 (see FIG. 31) can be deposited on the ITO layer or electrode 172 prior to same being bonded to the silicon nitride coated silicon block 166.

Figure 32A:
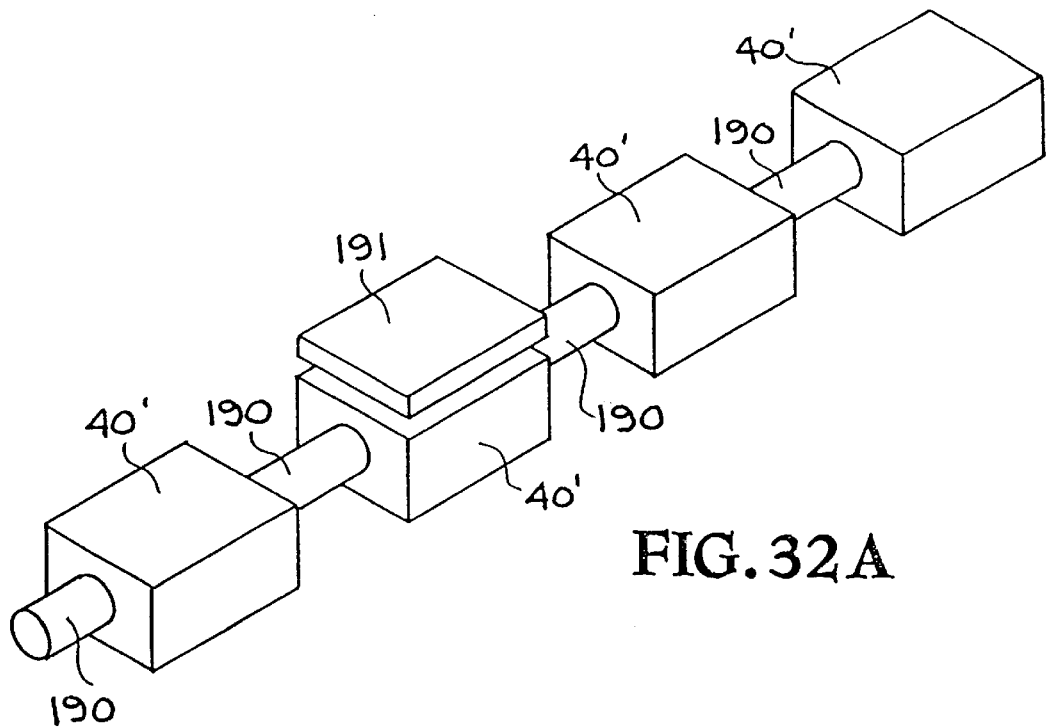
FIGS. 32A and 32B show linear and parallel multiple series of sleeve-type reaction chambers along a series of interconnecting tubes with reaction control, detection, and logic feedback units.
Figure 32B:
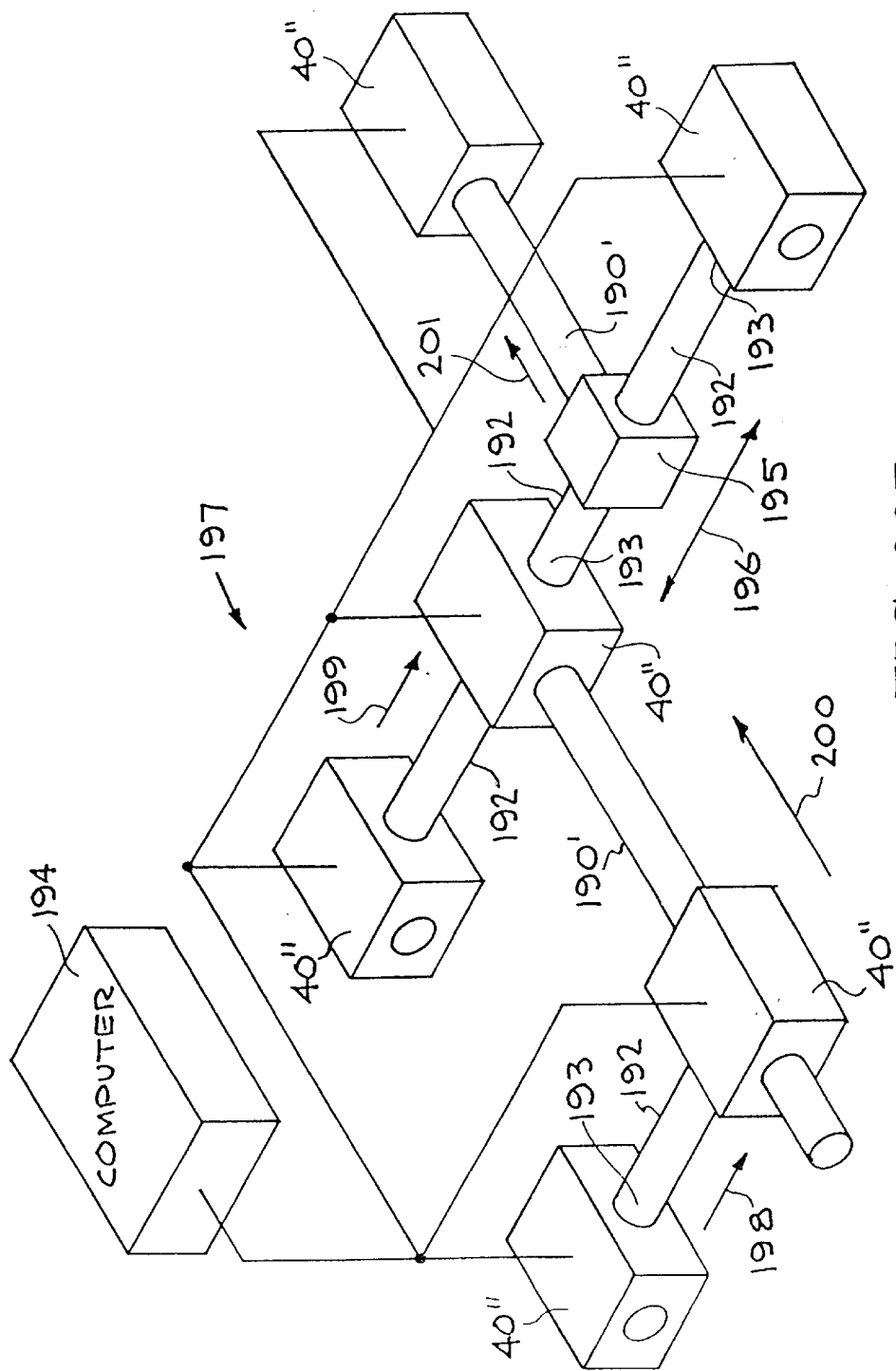

FIG. 32A illustrates a linear multiple series of sleeve-type reaction chambers 40' interconnected by tubes 190 extending from an end of one chamber to an end of a next chamber, and having an energy coupler 191 illustrated over only one of the reaction chambers 40' to form, a "string of beads" flow through reaction system. In operation the energy coupler 191 would be positioned on reaction chamber 40'. FIG. 32B illustrates a linear and parallel multiple series of sleeve-type reaction chambers 40' with interconnecting end to end tubes 190' as in FIG. 32A and interconnecting tubes 192 extending between openings 193 in the sides of the reaction chambers 40'. In FIG. 32B the reaction chambers are connected to a control, such as computer 194 and to a detector 195 to provide logic feedback as indicated by arrow 196, so as to produce a reaction element electronic control network indicated at 197, with net flow being indicated by arrows 198, 199, 200 and 201. This "string-of-beads? flow through reaction system is made up of interchangeable reaction chamber elements on a flow-through tubing system.

Figure 33A:
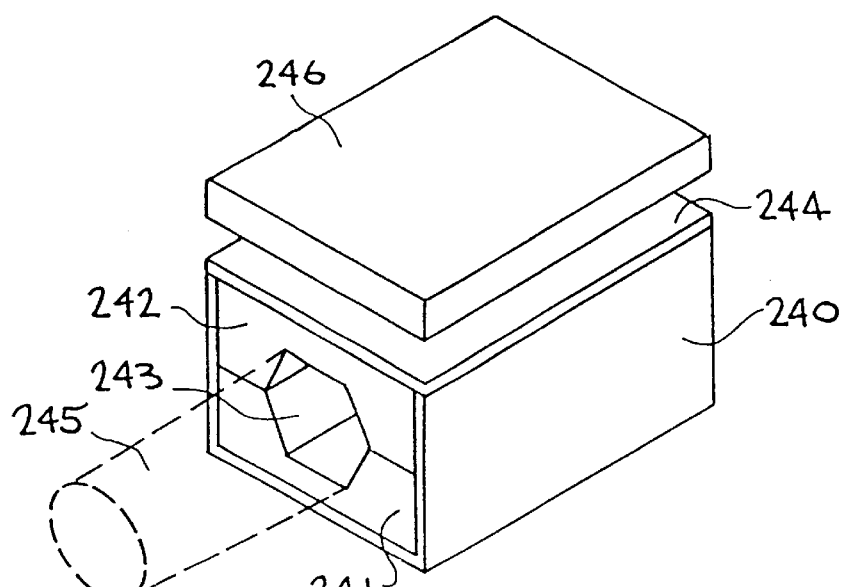
FIGS. 33A and 33B show embodiments of a reaction control unit that utilizes a micromachined (i.e., sputter-deposited) magnetic film to control magnetic particles in the reaction chamber.
Figure 33B:
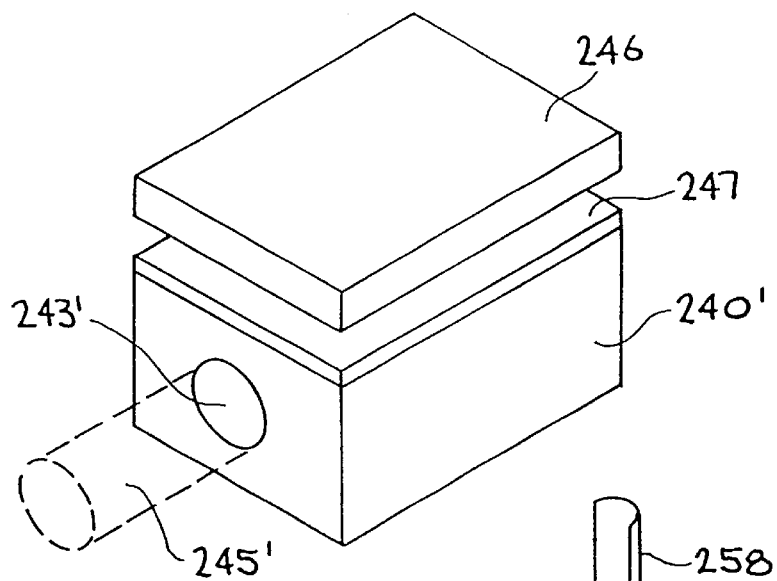

FIGS. 33A and 33B illustrate an embodiment of a reaction control units that utilize a micromachined (i.e., sputter-deposited) magnetic film to control magnetic particles in the sleeve reaction chamber. Other examples of micromachined elements are: electroactive films such as heaters, electrodes, thermoelectric and mechanical (i.e., shape memory) thin films, photodiodes, etc. The reaction chambers with integrated reaction control or detection element are coupled to an external energy source. FIG. 33A illustrates an embodiment of a sleeve-type reaction chamber 240 formed by two members 241 and 242 having an opening or slot 243 of six-sided configuration, with microfabricated control film 244 deposited thereon. A reaction chamber liner to tube connector 245 is connected in slot 243, and an energy coupler 246 is shown in spaced relation to control film 244, but in operation would be located on control film 244. The FIG. 33B embodiment differs from that of FIG. 33A in that the sleeve reaction chamber 240' is constructed of a single member and provided with a circular slot 243', whereby the tube connector 245' is cylindrical. Also, in the FIG. 33B embodiment, a microfabricated actuator 247 is located intermediate the reaction chamber 240' and an energy coupler 246. By way of example, the energy coupler in FIGS. 32A, 33A and 33B may be an electrode contact, radio frequency source, or an electrical contact to a DC energy source. Thusly, the individual reaction chambers 240 can be strung together as a series of different functionalities. For example, the series of modules could be a heated reaction chamber, followed by a magnetically actuated chamber, followed by a shape-memory or electrostatic pumping module. In this way the energy coupler could also be a way to connect to a series of energy sources. In the above example that could be an electrical contact to a DC source for resistive heating; a magnetic coil for magnetic actuation, and then an RF source to actuate the pumping mechanism.

Figure 34:
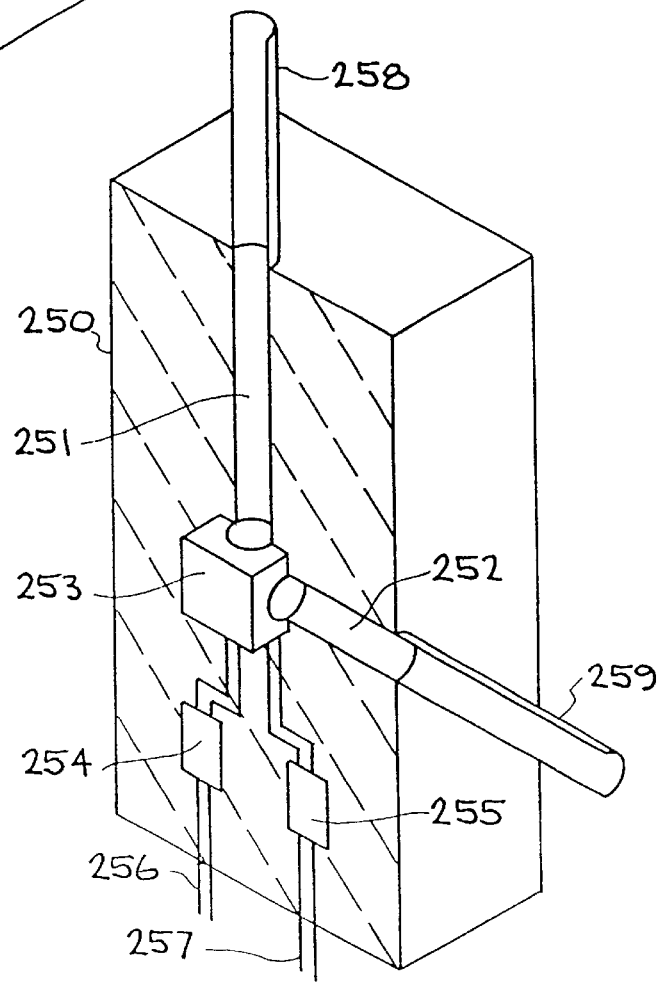
FIG. 34 illustrates the integration of a reaction control element in a monolithic flow-through system.

FIG. 34 illustrates the integration of a reaction element in a monolithic flow-through system. In this embodiment the micromachined element is placed within or adjacent to the block of material in which the flow channels are fabricated. As shown, a block of material 250, constructed for example of silicon, metal or polymer is provided with a pair of interconnected openings or passageways 251 and 252 with an embedded control element 253, such as a resistive thin-film heater; a magnetic film or coil; or a actuator such as an electrostatic pump, valve, or mixer, located at the intersection of passageways 251 and 252. A pair of control elements 254 and 255, are embedded in an outer surface of block 250 and operatively connected to embedded control element 253, with control leads 256 and 257 extending from block 250, for connection to control sources, such as a resistive thin-film heater; a magnetic film or coil; or a actuator such as an electrostatic pump, valve, or mixer. A pair of fluid interconnects 258 and 259 are connected to passageways or openings 251 and 252.

It has thus been shown that the present invention provides a silicon-based or non-silicon-based microreaction chamber which can be used in a hand-held instrument or a large high-throughput instrument. The sleeve reaction chamber may be made of various compatible materials or combinations of these materials. In addition, the invention provides for insert/liners, test strips, optical detection, and automatic control for the microreaction chamber. Thus, the present invention substantially advances the state of the art for PCR and other chemical reactions.

While particular embodiments, materials, parameters, etc. have been set forth to exemplify and explain the principles of the invention, such are not intended to be limiting. Modifications and changes may become apparent to those skilled in the art, and it is intended that the invention be limited only by the scope of the appended claims.

What is claimed is:

1. An apparatus for controlling the temperature of a reaction mixture contained in a tube or insert, the apparatus comprising:
   a) a reaction sleeve comprising at least two substrates defining a slot between them for receiving the insert, wherein the substrates are constructed of a material selected from the group consisting of ceramics, polymers, metals, metallic alloys, composites, or combinations thereof; and
   b) a resistive heater deposited on at least one of the substrates.

2. The apparatus of claim 1, wherein at least one of the substrates comprises a ceramic material, and wherein the heater comprises a film deposited on the ceramic material.

3. The apparatus of claim 1, wherein each of the substrates comprises a ceramic material, and wherein the apparatus includes at least one heater deposited on each of the ceramic substrates.

4. The apparatus of claim 1, wherein each of the substrates has a thickness in the range of 0.1 to 1.0 mm.

5. The apparatus of claim 1, wherein the ratio of the cross sectional area of the reaction sleeve to the cross sectional area of the slot is less than 5:1.

6. The apparatus of claim 1, wherein the ratio of the cross sectional area of the reaction sleeve to the cross sectional area of the slot is less than 3:1.

7. The apparatus of claim 1, wherein the ratio of the cross sectional area of the reaction sleeve to the cross sectional area of the slot is less than 2:1.

8. The apparatus of claim 1, wherein the sleeve includes a first optical window, the insert includes a second optical window which is aligned with the first window when the insert is positioned in the sleeve, and the apparatus further comprises an optical detector for detecting a product in the reaction mixture through the windows.

9. The apparatus of claim 8, wherein the second window includes a test strip.

10. The apparatus of claim 8, further comprising:
    a) a data readout system connected to the detector; and
    b) an instrument controller connected to the data readout system.

11. The apparatus of claim 10, wherein each of the substrates comprises a ceramic material, and wherein the apparatus includes at least one heater deposited on each of the ceramic substrates.

12. The apparatus of claim 11, wherein each of the ceramic substrates has a thickness in the range of 0.1 to 1.0 mm.

13. The apparatus of claim 1, wherein the heater comprises a thermoelectric film.

14. The apparatus of claim 11, further comprising an electroactive film coupled to at least one of the substrates for controlling an electrically active reagent in the reaction mixture.

15. The apparatus of claim 11, further comprising a magnetic film coupled to at least one of the substrates for controlling a magnetic or paramagnetic reagent in the reaction mixture.

16. The apparatus of claim 1, further comprising a hand-held, battery-operated instrument into which the sleeve is inserted, wherein the instrument includes electronics for controlling the heater.

17. The apparatus of claim 1, further comprising an array of such reaction sleeves and an instrument for holding the sleeves, wherein the instrument includes control elements for individually controlling the operation of each sleeve.

18. The apparatus of claim 1, further comprising an array of such reaction sleeves and an array of adjacent detectors for providing feedback control of a reaction process in the sleeves.

19. An apparatus for controlling the temperature of a reaction mixture, the apparatus comprising:
    a. a reaction sleeve defining a chamber for receiving the mixture, wherein the sleeve has at least one open end for insertion of the mixture into the chamber, and wherein the sleeve is constructed of a material selected from the group consisting of ceramics, polymers, metals, metallic alloys, composites, or combinations thereof; and
    b. at least one resistive heater deposited on the sleeve for heating the mixture contained in the chamber, wherein the ratio of the cross sectional area of the sleeve to the cross sectional area of the chamber is less than 5:1.

20. The apparatus of claim 19, further comprising an insert for holding the mixture, wherein the insert is constructed of a material that is substantially inert with respect to the mixture, and wherein the insert is sized to be inserted into the chamber.

21. The apparatus of claim 20, wherein the sleeve includes a first optical window, the insert includes a second optical window which is aligned with the first window when the insert is positioned in the chamber, and the apparatus further comprises an optical detector for detecting a product in the reaction mixture through the windows.

22. The apparatus of claim 21, further comprising:
    a. a data readout system connected to the detector; and
    b. an instrument controller connected to the data readout system.

23. The apparatus of claim 19, further comprising a liner inside the sleeve, wherein the liner comprises a material that is substantially inert with respect to the reaction mixture.

24. The apparatus of claim 19, wherein the sleeve comprises a ceramic material, and wherein the heater comprises a film deposited on the ceramic material.

25. The apparatus of claim 19, wherein the sleeve comprises at least two substrates defining the chamber between them, and wherein the apparatus includes at least one heater deposited on each of the substrates.

26. The apparatus of claim 25, wherein each of the substrates has a thickness in the range of 0.1 to 1.0 mm.

27. The apparatus of claim 25, wherein each of the substrates comprises a ceramic material.

28. The apparatus of claim 19, wherein the ratio of the cross sectional area of the sleeve to the cross sectional area of the chamber is less than 3:1.

29. The apparatus of claim 19, wherein the ratio of the cross sectional area of the sleeve to the cross sectional area of the chamber is less than 2:1.

30. The apparatus of claim 19, further comprising a hand-held, battery-operated instrument into which the sleeve is inserted, wherein the instrument includes electronics for controlling the heater.

31. The apparatus of claim 19, further comprising an array of such reaction sleeves and an instrument for holding the sleeves, wherein the instrument includes control elements for controlling the operation of the sleeves.

32. The apparatus of claim 31, further comprising a microelectrophoresis array, wherein the array of reaction sleeves is connected to the microelectrophoresis array.

33. The apparatus of claim 32, further comprising at least one array of microinjectors connecting the array of reaction sleeves to the microelectrophoresis array.

34. The apparatus of claim 19, wherein the heater comprises at least one film.

35. The apparatus of claim 19, further comprising an electroactive film coupled to the sleeve for controlling an electrically active reagent in the reaction mixture.

36. The apparatus of claim 19, further comprising a magnetic film coupled to the sleeve for controlling a magnetic or paramagnetic reagent in the reaction mixture.

37. The apparatus of claim 19, further comprising an array of such reaction sleeves and tubes connecting the chambers of the sleeves to each other to provide a flow-through reaction system.

38. The apparatus of claim 37, further comprising an array of detectors for providing feedback control of a reaction process in the sleeves.

39. An apparatus for controlling the temperature of a reaction mixture contained in a tube or insert, the apparatus comprising:
    a. a reaction steere comprising at least two substrates defining a slot between them for receiving the insert, wherein the substrates are constructed of a material selected from the group consisting of ceramics, polymers, metals, metallic alloys, composites, or combinations thereof, and wherein each of the substrates has a thickness in the range of 0.1 to 1 mm; and
    b. a heater coupled to at least one of the substrates for heating the mixture contained in the insert.

40. The apparatus of claim 39, wherein each of the substrates comprises a ceramic material, and wherein the apparatus includes at least one resistive heater deposited on each of the ceramic substrates.

41. The apparatus of claim 40, wherein each of the heaters comprises a film.

42. The apparatus of claim 39, wherein the steere comprises a first optical window, the insert includes a second optical window which is aligned with the first window when the insert is positioned in the sleeve, and the apparatus further comprises an optical detector for detecting a product in the reaction mixture through the windows.

43. The apparatus of claim 42, further comprising:
   a. a data readout system connected to the detector; and
   b. an instrument controller connected to the data readout system.

44. In a microfabricated chemical reactor, the improvement comprising:
   a. an insert for holding a reaction fluid; and
   b. a sleeve reaction chamber comprising at least two substrates defining a slot between them for receiving the insert; wherein the substrates are constructed of a material selected from the group consisting of ceramics, polymers, metals, metallic alloys, composites, or combinations thereof; and the sleeve reaction chamber includes at least one heating element for heating the reaction fluid.

45. The improvement of claim 44, wherein the sleeve reaction chamber comprises a ceramic material, and wherein the heating element comprises a resistor coupled to the ceramic material.

46. The improvement of claim 44, wherein the insert includes an optical window, and wherein the chemical reactor further comprises an optical detector positioned adjacent the optical window.

* * * * *